United States Patent [19]

Meryman et al.

[11] Patent Number: 5,250,303
[45] Date of Patent: Oct. 5, 1993

[54] PROCEDURE FOR STORING RED CELLS WITH PROLONGED MAINTENANCE OF CELLULAR CONCENTRATIONS OF ATP AND 2,3 DPG

[75] Inventors: Harold T. Meryman, Sandy Spring, Md.; Marne Hornblower, Washington, D.C.; Ralph Syring, Silver Spring, Md.

[73] Assignee: The American National Red Cross, Washington, D.C.

[21] Appl. No.: 594,152

[22] Filed: Oct. 9, 1990

Related U.S. Application Data

[63] Continuation-in-part of Ser. No. 417,761, Oct. 6, 1989, abandoned.

[51] Int. Cl.$^5$ .............................................. A61K 35/18
[52] U.S. Cl. .................................. 424/533; 424/529; 435/2
[58] Field of Search ................... 435/2; 424/533, 529

[56] References Cited

U.S. PATENT DOCUMENTS

| | | |
|---|---|---|
| 4,112,070 | 9/1978 | Harmening . |
| 4,427,777 | 1/1984 | Goldstein et al. . |
| 4,585,735 | 4/1986 | Meryman et al. ................ 435/2 |

FOREIGN PATENT DOCUMENTS

| | | |
|---|---|---|
| 0301250 | 1/1989 | European Pat. Off. . |
| 0152719 | 12/1981 | German Democratic Rep. . |
| 63-063616 | 3/1988 | Japan . |
| WO86/06585 | 11/1986 | PCT Int'l Appl. . |

OTHER PUBLICATIONS

Mueller et al.—Chem. Abstr. vol. 100 (1984) p. 207,088p.
Minakami, S. et al., In *Erythrocyte Structure and Function* (Brewer, C. D. Ed.) New York, Liss, pp. 149-166 (1975).
Moore et al. Post-Thaw Storage at 4° C. of Previously Frozen Red Cells with Retention of 2,3 DPG. *Vox Sang.* 53: 15-18 (1987).
Carmen, R. A., et al., Five-week red cell storage with Preservation of 2,3 DPG. *Transfusion* 28: 157-161 (1988).
Meryman, H. T., Influence of Certain Neutral Solutes on Red Cell... *Amer. J. Physiol.* 225(2): 365-371 (1973).

*Primary Examiner*—Sam Rosen
*Attorney, Agent, or Firm*—Sterne, Kessler, Goldstein & Fox

[57] ABSTRACT

This invention provides an improved method for prolonging the shelf life of transfusible red blood cells by decreasing the effective osmolality of the suspending solution and increasing the intracellular pH of the cells prior to storage thereof. This invention also provides methods whereby the intracellular pH may be increased. These methods include collecting the cells in an anticoagulant at pH 7.0 or higher and/or washing, diluting or resuspending the cells prior to storage thereof in a biologically compatible buffered solution that contains at least one non-penetrating or substantially non-penetrating anion or non-electrolyte and is substantially free of chloride ions.

14 Claims, 17 Drawing Sheets

PROCEDURE FOR STORING RED CELLS WITH PROLONGED MAINTENANCE OF CELLULAR CONCENTRATIONS OF ATP AND 2,3 DPG

This application is a continuation-in-part of U.S. patent application Ser. No. 07/417,761, which was filed on Oct. 6, 1989, now abandoned, the contents of which are herein incorporated by reference.

BACKGROUND OF INVENTION

There are two general methods for the refrigerated storage of human red blood cells: 1) refrigerated storage in the original anticoagulant solution; 2) refrigerated storage after separation of the red cells from the anticoagulant solution and the plasma, and resuspension of the cells in a solution that is specifically designed for red cell storage.

1) For storage in the original anticoagulant, whole blood is conventionally drawn into a solution containing citrate, phosphate, dextrose (d-glucose) and adenine (CPDA-1) at pH 5.7. The blood is centrifuged at about 1500 g (soft spin) and the plasma removed leaving a red cell suspension with an hematocrit of about 75%. Platelets can be removed from the plasma by a second sedimentation.

2) For resuspension of the red cells and storage in a preservation solution, blood is conventionally drawn into a solution containing only citrate, phosphate and glucose at pH 5.7. The blood is centrifuged at the same speed as described in (1) above but the red cells are then resuspended in either Adsol of Nutricel (see Table at pH 5.7 and 5.8 respectively, resulting in a red cell suspension at an hematocrit of approximately 55%.

During storage, human red blood cells undergo morphological and biochemical changes, including decreases in the cellular levels of adenosine triphosphate (ATP) and 2,3 diphosphoglycerate (2,3 DPG), changes in cellular morphology and progressive hemolysis. The concentration of ATP, after a brief initial rise, progressively declines to between 30 and 40% of its initial level after six weeks of storage. The fluidity of the cell membrane of red cells, which is essential for the passage of red cells through the narrow channels in the spleen and liver, is loosely correlated with the level of ATP. The level of 2,3 DPG falls rapidly after about 3 or 4 days of storage and approaches zero by about 10 days. 2,3 DPG is associated with the ability of the hemoglobin in the red cells to deliver oxygen to the tissues. Morphological changes occur during storage, ultimately leading to the development of spicules on the cells (echinocytosis). These spicules can bud off as vesicles, radically changing the surface-to-volume ratio of the cells and their ability to deform on passing through narrow channels. Such cells will be filtered out of the circulation by the spleen and liver following transfusion. To be acceptable for transfusion at least 75% of the red cells that are transfused must be circulating 24 hours following the transfusion. Shelf life of red blood cells is determined on this basis. The concentration of ATP and the morphology of red cells serve as indicators of the suitability of stored cells for transfusion.

In order to prolong the shelf life of transfusible red blood cells it is necessary to store the cells or treat them in some manner that prevents a rapid decline in ATP and, if possible, 2,3 DPG (see e.g., Harmening, U.S. Pat. No 4,112,070 and Goldstein, U.S. Pat. No. 4,427,777). Solutions that prolong the shelf life of red cells are known (see e.g., Harmening, supra. and Meryman, U.S. Pat. No. 4,585,735, which disclosure is herein incorporated in its entirety by reference thereto). Typically such solutions contain citrate, phosphate, glucose and adenine and occasionally other ingredients that function to prolong shelf life by maintaining the level of ATP in the cells. Minakami et al. ((1975) In: Brewer, C. J., ed. *Erythrocyte Structure and Function,* New York, Liss, pp. 149-166) report that glycolytic activity is enhanced in red blood cells if the intracellular pH (hereinafter $pH_i$) measured at 4° C. is about 7.4 and suggest that $pH_i$ is a parameter that should be considered with respect to blood preservation. Solutions that maintain high levels of both ATP and 2,3 DPG, during long term storage without artificial intervention (see, e.g. Harmening, supra.) or without the inclusion of compounds such as ammonium, not licensed for transfusion (see, e.g., Meryman, supra.), are not, however, known.

Procedures and solutions have been devised that permit some of the declines in ATP and 2,3 DPG and the morphological changes associated with long-term storage to be reversed and thereby rejuvenate the red blood cells. Rejuvenating solutions, however, are not suitable for transfusion; they must be removed prior to transfusing the cells. There is, thus, a risk of contamination associated with this procedure. Federal law requires that cells that have been so-treated must be transfused within 24 hours in order to minimize the risk of bacterial growth. Devices have now been developed that permit removal of the rejuvenation solution in a closed system without subjecting the cells to the risk of contamination. However, after rejuvenation the cells must be washed with a solution that is suitable for transfusion. Conventional wash solutions, such as glucose-saline solutions, are not, however, suitable for storage beyond 24 hours.

There are other instances in which red blood cells must be washed. For example, cells that are stored by freezing in glycerol must be deglycerolized by washing prior to use. Moore et al. (1987, *Vox Sang.* 53:19–22) have reported deglycerolizing frozen red cells using a phosphate-buffered sodium chloride wash solution with resuspension in a solution containing adenine, ascorbate-2-phosphate, trisodium phosphate, dextrose and mannitol at a pH of 11.0 and an osmolality of 446 mOsm. Both ATP and 2,3 DPG were adequately maintained for 21 days. However, ascorbate-2-phosphate has not been licensed for use in a solution for transfusion. In a subsequent publication, Carmen et al. (1988, *Transfusion* 28:157-161) reported that red cells stored for only 5 weeks in a solution containing ascorbate-2-phosphate lost ATP to a level of 22.2% of initial value with 24-hour survival falling below 75%.

Red blood cells that have been subjected to other treatments must also be washed prior to transfusion. For example, Goldstein, supra., discloses a method for converting type B red cells into type O cells by removing the terminal galactose moiety of the B-antigenic determinant of stroma from type A cells under conditions wherein the cells do not lose their cellular functions so that they are suitable for transfusion. The enzymatic cleaving of the terminal galactose must be performed at low pH. Following enzymatic treatment the red cells are washed with isotonic sodium chloride that is buffered with 0.01M potassium phosphate buffer at pH 7.4 in part to wash out residual enzyme and in part to raise the pH. Cellular metabolic studies indicate that ATP levels remain above 90% and 2,3 DPG levels are 80-90% immediately after this treatment, but these levels would not be maintained during subsequent storage in this washing solution.

Transfusion of red blood cells poses a risk of viral infection in a recipient from blood that has been obtained from donors that are infected with viruses, such as non A non B hepatitis virus and human immunodeficiency virus. In order to mitigate this risk procedures have been reported whereby the cells are treated with agents that inactivate the viruses. Red cells that are detoxified, however, must then be washed in order to remove the inactivating agent in order to render them suitable for transfusion. No resuspension solution is available that will permit subsequent storage of such cells.

In certain circumstances it is desirable to extend the shelf-life of refrigerated red cells beyond the current 42 days. Autologous units drawn for use in elective surgery may expire before the surgery can be performed. It has also been proposed that blood be stored for several months to permit retesting the donor for evidence of AIDS or hepatitis infection. Other than by freezing, which is labor intensive and expensive, no such capability is known to exist.

Because of the critical need for transfusible red blood cells, it is of great importance to develop methods and solutions that not only maintain high intracellular levels of both ATP and 2,3 DPG, good morphology and low hemolysis after washing but also to develop methods for the routine collection and resuspension of unwashed red cells with better storage characteristics than are achieved by current procedures. Further there is a need to develop solutions that are suitable for both washing and storing transfusible red blood cells.

A great need in the art is to develop procedures for storing red blood cells after collection, but without washing; such a method would have substantial clinical importance.

It is also desirable that the quantity of adenine in transfusable red cells be reduced or eliminated because of concern regarding their nephrotoxicity.

SUMMARY OF THE INVENTION

This invention provides an improved method for prolonging the storage shelf life of transfusible red blood cells either with or without preliminary washing, comprising: increasing the intracellular pH of said cells to a level that is comparable to or higher than the normal physiological level thereof (pH 7.4@22° C.); and storing said cells in a biologically compatible buffered solution that is hypotonic with respect to solutes that do not penetrate the cells and that is clinically acceptable for transfusion.

The invention also provides methods for raising the intracellular pH of red blood cells prior to storage.

This invention further provides a method for prolonging the shelf life of transfusible red blood cells, comprising washing and storing said cells in a functionally hypotonic, biologically compatible buffered solution that is substantially free of chloride and that contains at least one substantially non-penetrating solute.

The invention provides an improved method for prolonging the shelf life of transfusible red blood cells, comprising decreasing the intracellular concentration of chloride in said cells.

This invention provides a method for prolonging the shelf life of transfusible red blood cells, comprising washing said cells with a biologically compatible buffered solution that raises the intracellular pH of said cells to a level that is higher than the normal physiological level thereof, which is 7.4.

A method is also provided for prolonging the shelf life of red blood cells, comprising diluting the cells with a biologically compatible buffered solution to a low hematocrit, whereby the shelf life of the red blood cells is increased compared to the shelf life of red blood cells stored in the same buffer at a hematocrit of about 55%.

The invention also reduces or eliminates the requirement for adenine as a component of a red cell preservation solution.

This invention significantly improves the procedure for storing red blood cells—with or without a prior wash—by providing methods that lead to reduction or elimination of adenine from the storage solution, improvement of red cell morphology, reduction of hemolysis, increases in the intracellular levels of ATP and 2,3 DPG and maintenance of said levels at or above physiological concentrations for extended periods of time.

In practicing this invention the shelf life of red blood cells is significantly improved compared to the shelf life of red blood cells that are stored using prior art methods.

BRIEF DESCRIPTION OF THE FIGURES

FIGS. 3 and 4 demonstrate the superiority of red cell storage in a high pH solution but FIG. 1 through 4 also demonstrates the critical importance of reducing the chloride concentration.

Figure 7:
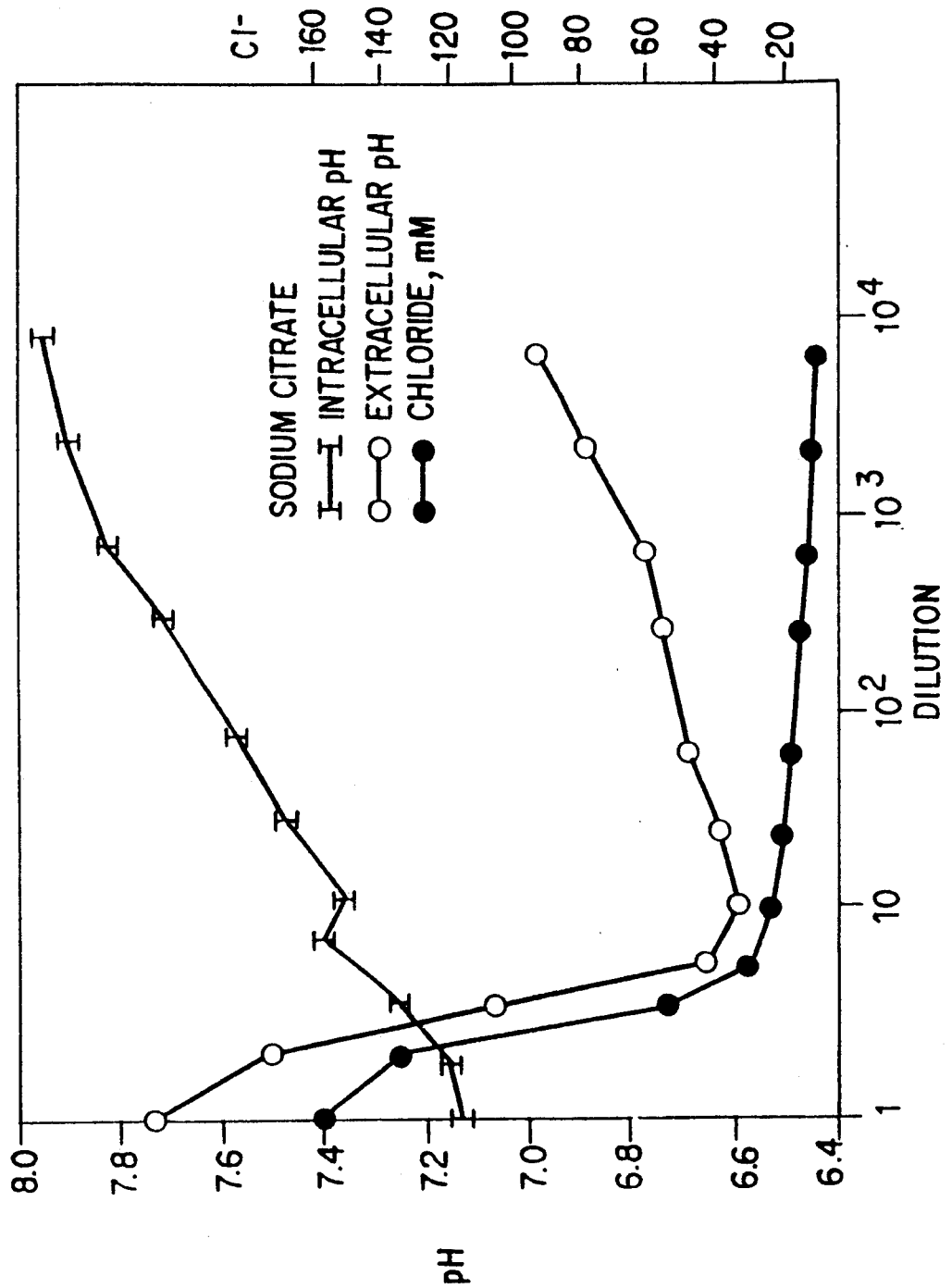

FIG. 7 shows the changes in the extracellular pH, -0--0--0-, and the intracellular pH, -I--I-, as the cells are successively washed with washes containing isotonic sodium citrate, adjusted to pH 7.4. As the cells are washed, diffusible ions, such as chloride are diluted and, thereby, decrease in concentration. The maximum differential between intracellular pH and extracellular pH was observed when the chloride concentration had been diluted to about 10% of its original value.

Figure 8:
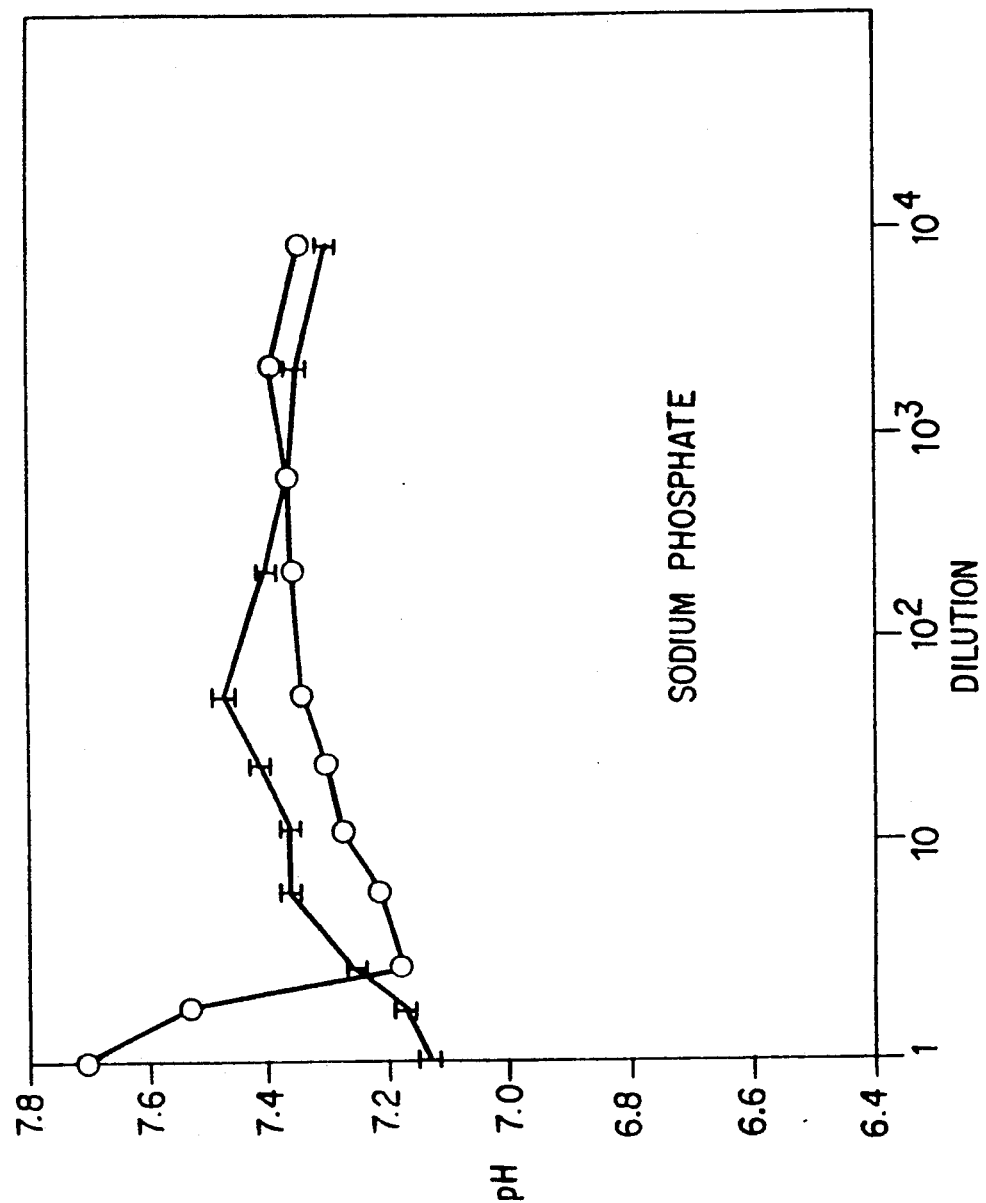

FIG. 8 shows the changes in the extracellular pH, -0--0--0-, and the intracellular pH, -I--I-, as the cells are progressively washed with isotonic sodium phosphate, adjusted to pH 7.4. Because phosphate is not fully excluded by the cellular membrane, this wash solution does not produce a differential between the intracellular pH and the extracellular pH. However, because sodium phosphate has good buffering capacity in the pH range of 7.0 to 8.0, the level of intracellular pH is raised to that of the wash solution.

Figure 9:
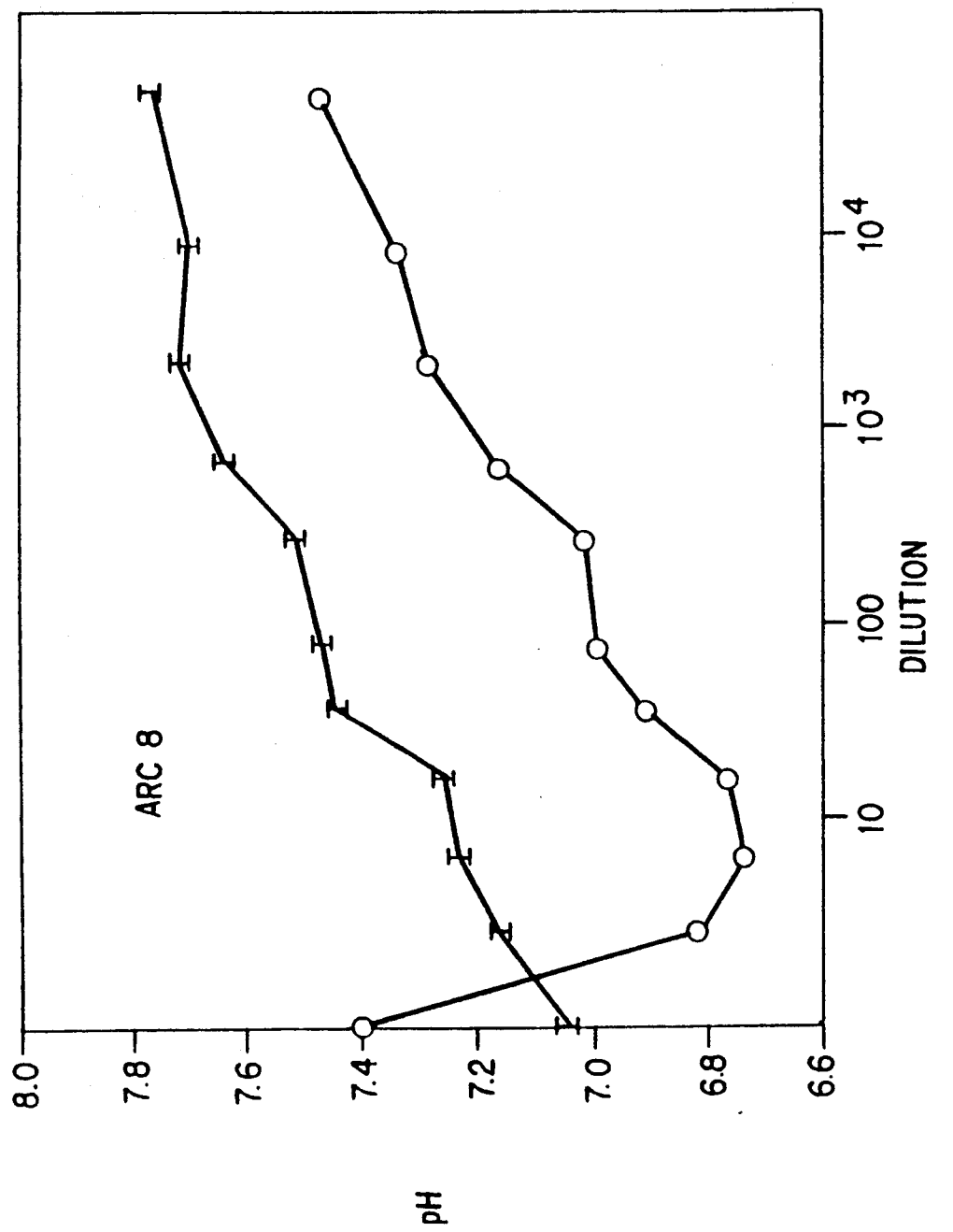

FIG. 9 illustrates the pH effect of washing cells with a solution (ARC8) that combines the benefits of citrate in inducing chloride shift (see FIG. 7) and the benefits of phosphate in supporting both intra and extracellular pH (see FIG. 8). Intracellular pH -I--I--I-, extracellular pH -0--0--0-.

Figure 10:
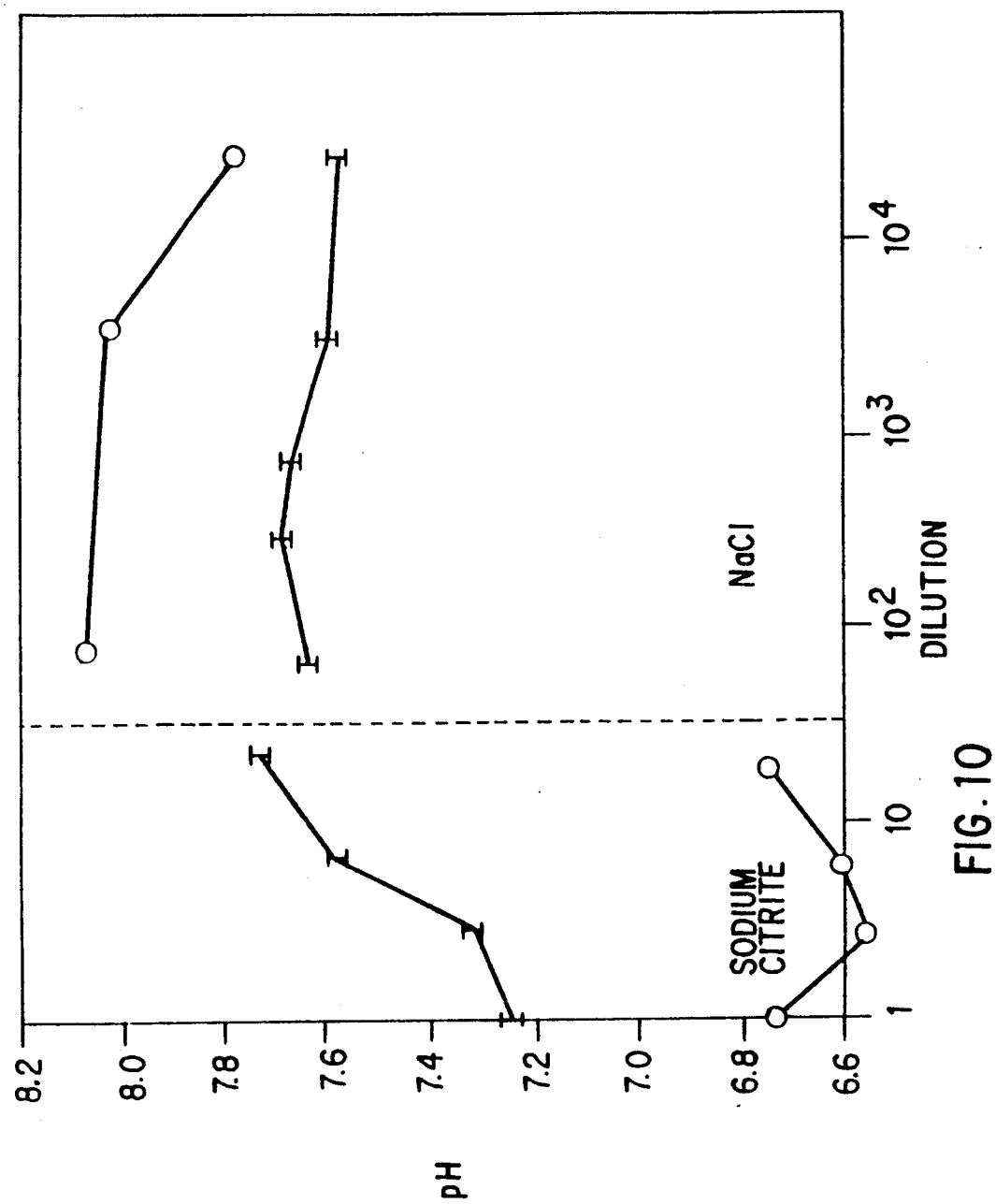

FIG. 10 shows the effect on the extracellular pH, -0--0--0-, and the intracellular pH, -I--I-, of an initial wash with phosphate-buffered isotonic sodium citrate adjusted to pH 7.4, followed by a sodium chloride wash. The initial citrate wash is the critical step in establishing a high intracellular pH. Since it elevates the pH of hemoglobin which is a strong buffer in the range pH 7.0 to 8.0 $pH_i$ is thereby maintained even after the chloride shift is reversed by the reintroduction of chloride.

Figure 11:
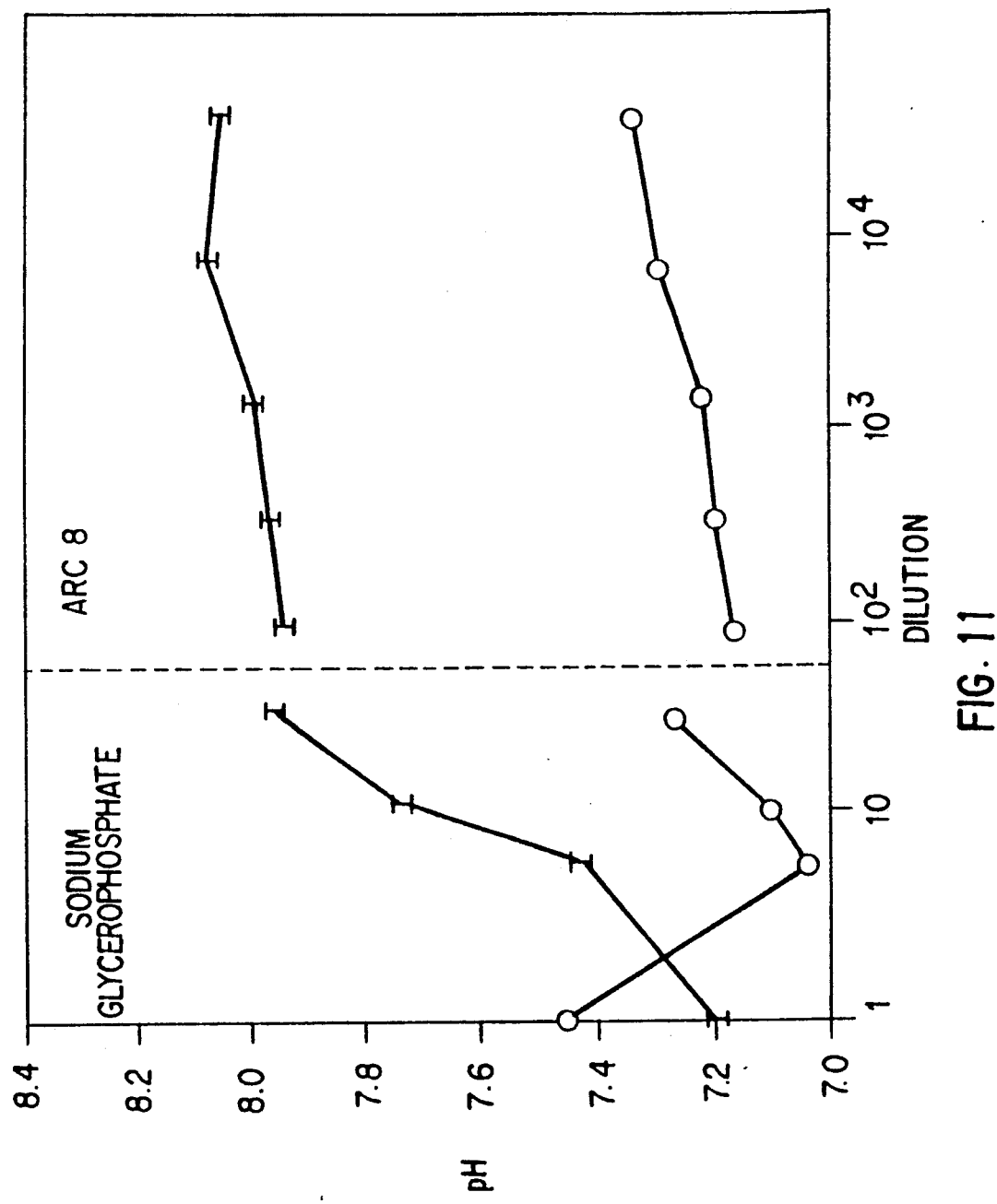

FIG. 11 shows the effect on the extracellular pH, -0--0--0-, and the intracellular pH, -I--I-, of initial washing with isotonic sodium glycerophosphate, pH 9.5, followed by washing in ARC8. Glycerophosphate is a good buffer in the range 7.0-8.0 as well as being non-penetrating, making it an ideal solute for red cell washing since it will maximize the chloride shift and concurrently elevate extracellular pH, further elevating intracellular pH. Since glycerophosphate is not currently licensed for use in a transfusible solution, it could be washed out with ARC8 without losing the benefit of the high $pH_i$.

Figure 12:
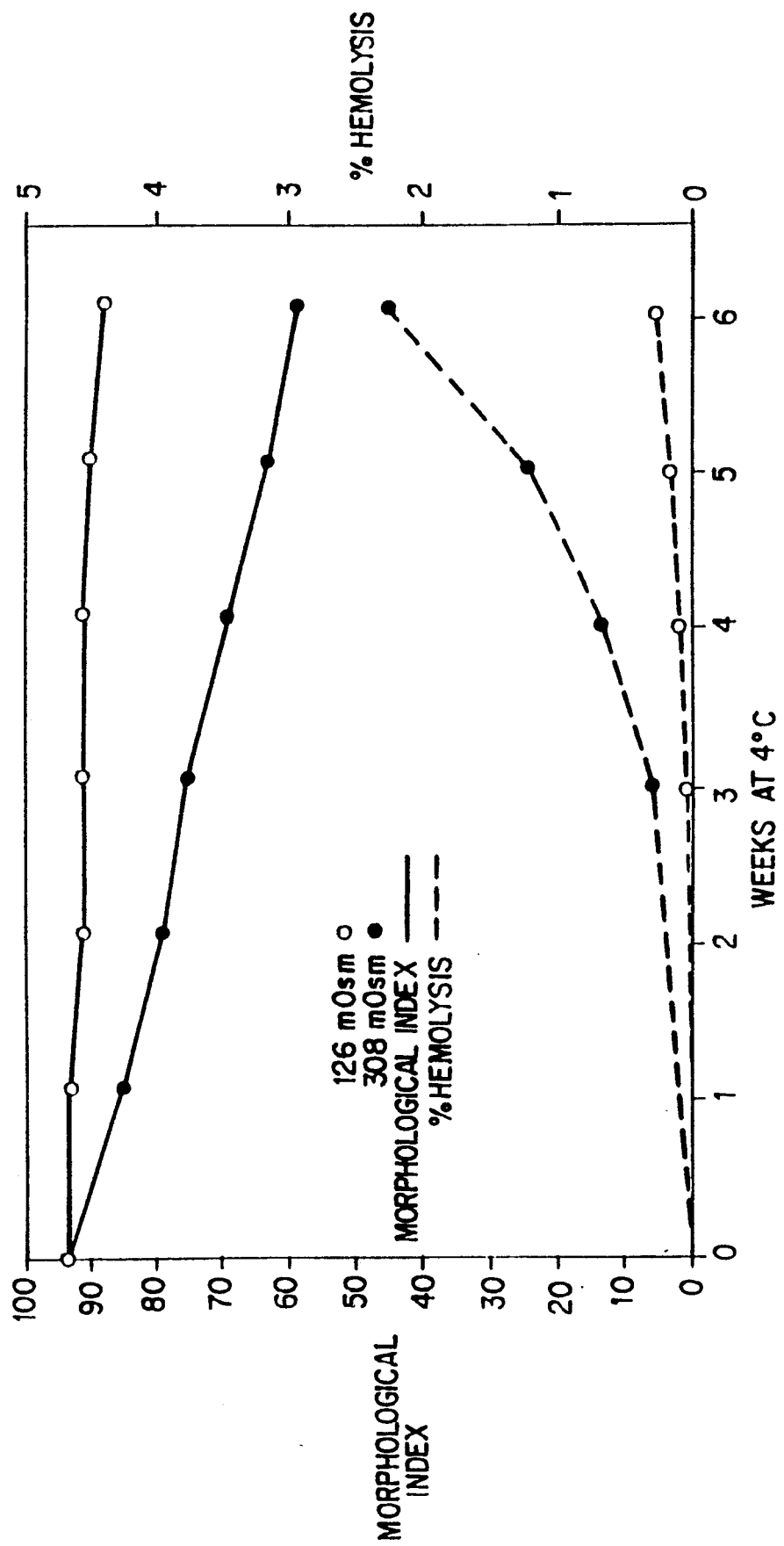

FIG. 12 illustrates the beneficial effects of effective hypotonicity on the morphological index and hemolysis during storage of red cells. Half a unit of red cells was washed and stored in ARC8 which has an effective osmolality of 126 mOsm (excluding the osmolality of glucose which penetrates the cells and therefore has no effect on cell volume). The other half of the unit was stored in ARC8 to which mannitol was added to render the effective osmolality isotonic at 308 mOsm. Despite mannitol's reputation for preventing hemolysis of red cells during storage, both hemolysis and morphology were poorer in the isotonic solution.

Figure 13:
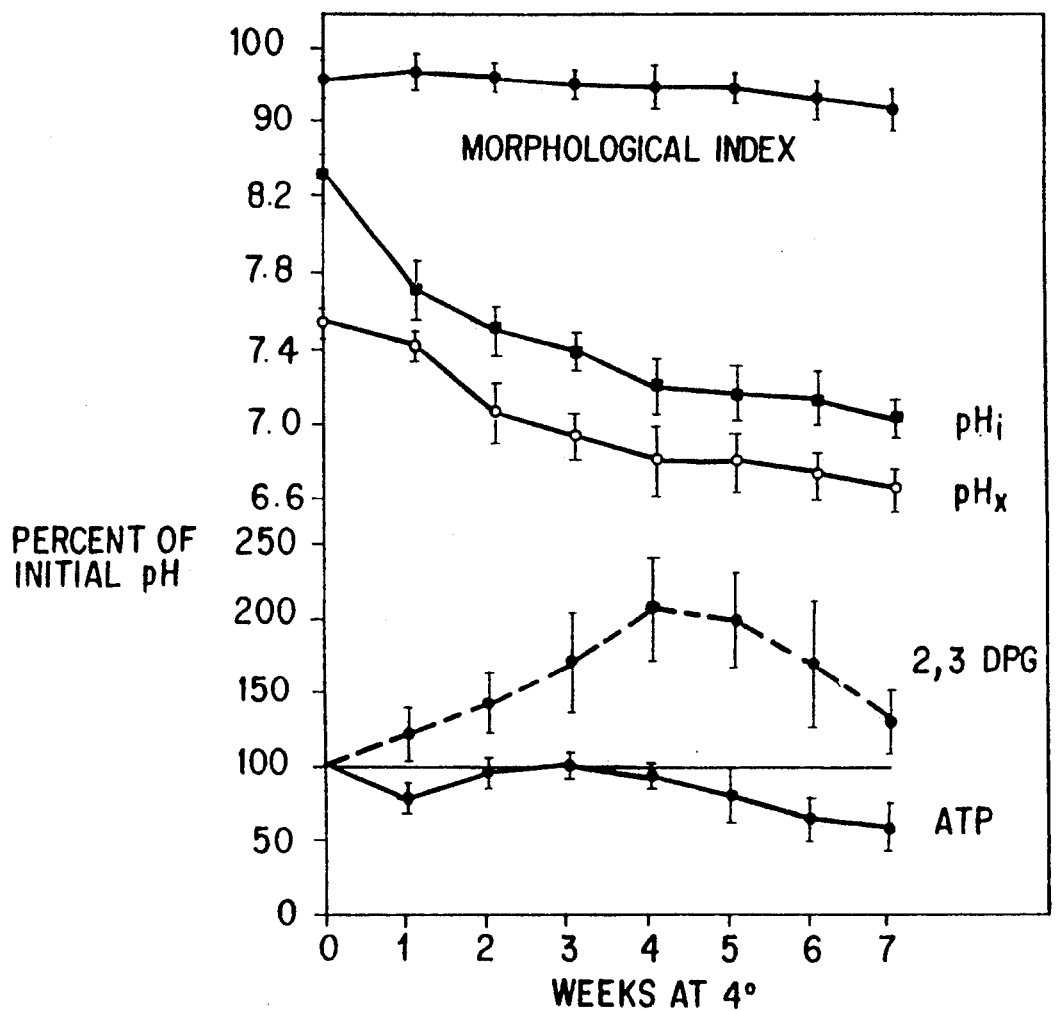

FIG. 13 depicts the mean morphological index, the intracellular pH ($pH_i$), and the extracellular pH ($pH_x$), measured at 4° and the percentage of initial intracellular concentrations of 2,3 DPG and ATP of six units of red cells both washed and stored for seven weeks at an hematocrit of 55%. This illustrates the superior storage possible utilizing the principles of this invention. No red cell storage procedure has been reported that can result in prolonged elevation of both ATP and 2,3 DPG as well as morphological index above 90% at seven weeks.

Figure 14:
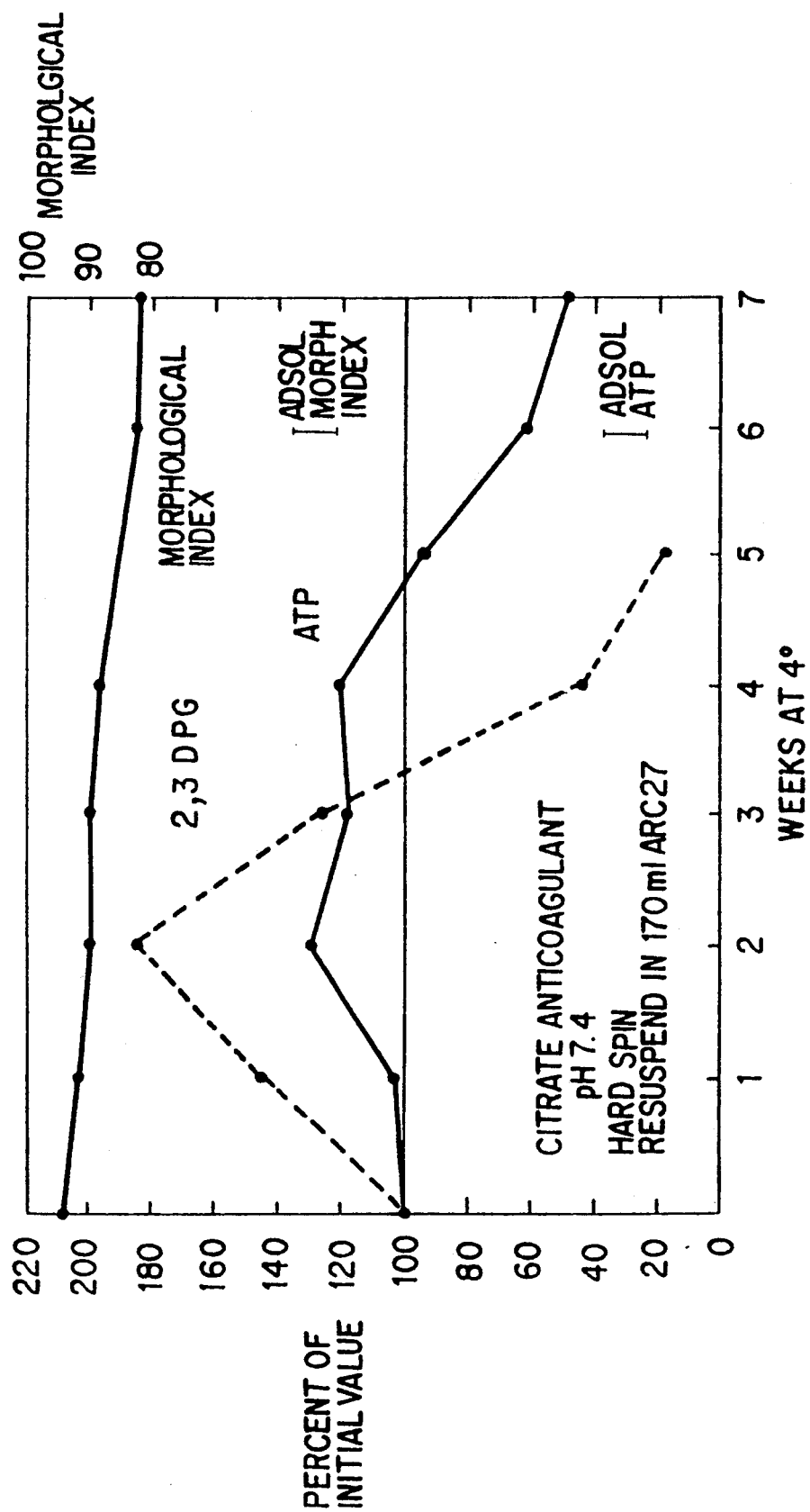

FIG. 14 depicts the morphological index, the percentage of hemoloysis, and the percentage of initial intracellular concentrations of 2,3 DPG and ATP as a function of weeks of storage at 4° C. in ARC27 for a unit of red blood cells that was drawn into 63 ml of sodium citrate anticoagulant at pH 7.4, spun down at about 7300 g (hard spin) for ten minutes to an hematocrit of 98% and resuspended in 170 ml ARC27, pH 7.4. The initial $pH_i$ of the unit at 4° was 7.87. The chloride concentration was 34 mM. This figure shows that the benefits achieved by washing out chloride with non-penetrating solute and/or a good buffer in the pH range 7.0-8.0 can to a considerable extent be achieved without washing by reducing chloride concentration by minimizing the carry-over of plasma by maximizing red cell hematocrit with a hard spin prior to resuspension. No currently used or reported red cell storage protocol can achieve this quality of ATP, 2,3 DPG and morphology during 4° storage. By way of comparison, the morphological index and ATP levels normally seen in red cells preserved for six weeks in conventional fashion in Adsol are shown. 2,3 DPG in Adsol approaches zero in 10 to 14 days.

Figure 15:
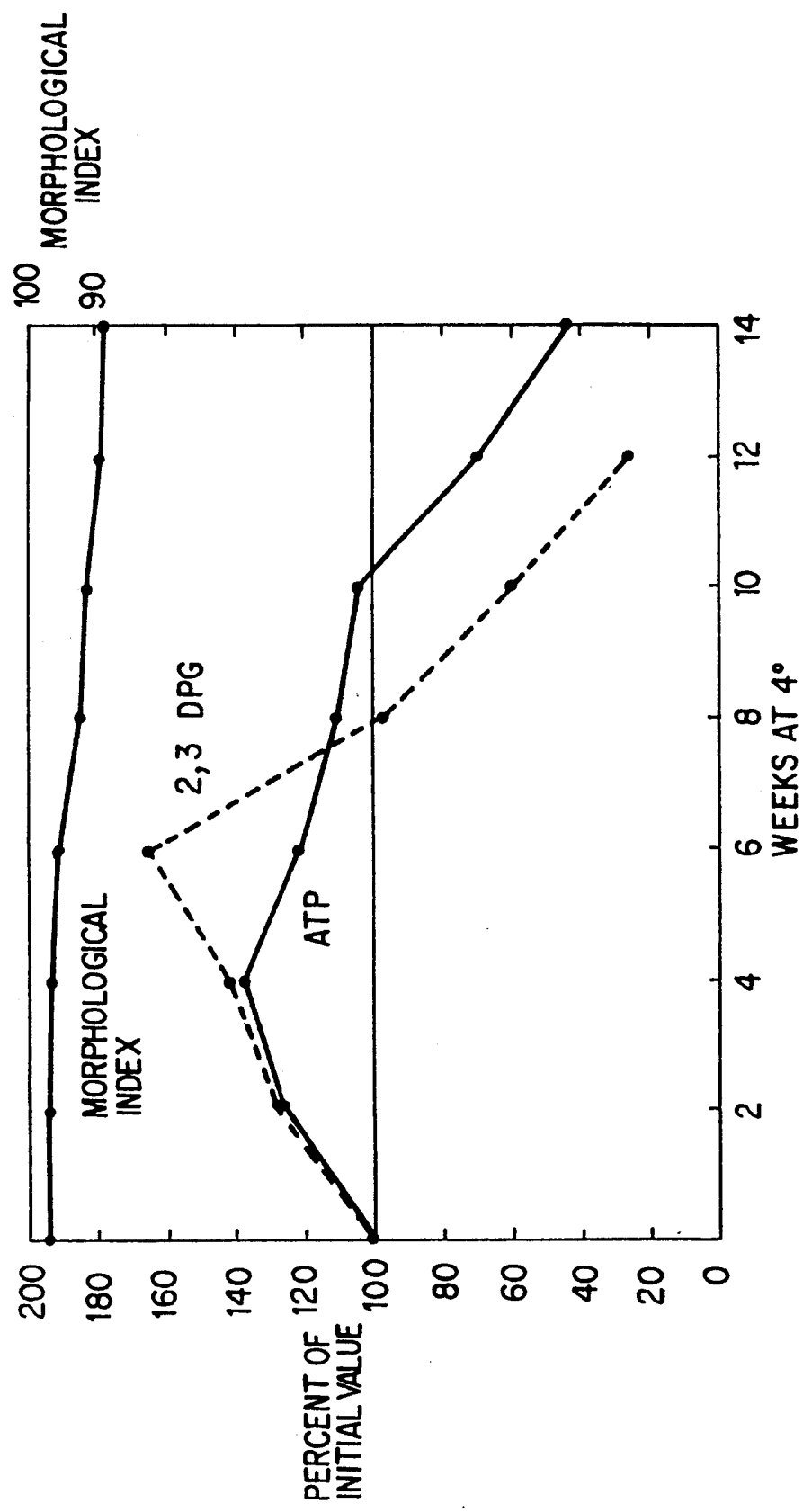

FIG. 15 depicts the morphological index, the percentage of hemolysis, and the percentage of initial intracellular concentrations of 2,3 DPG and ATP as a function of weeks of storage at 4° C. at an hematocrit of 10% of red cells diluted with and stored in the presence of 2 liters of ARC30. The greater quantity of buffer prolongs the maintenance of ATP and 2,3 DPG to at least 14 weeks.

Figure 16:
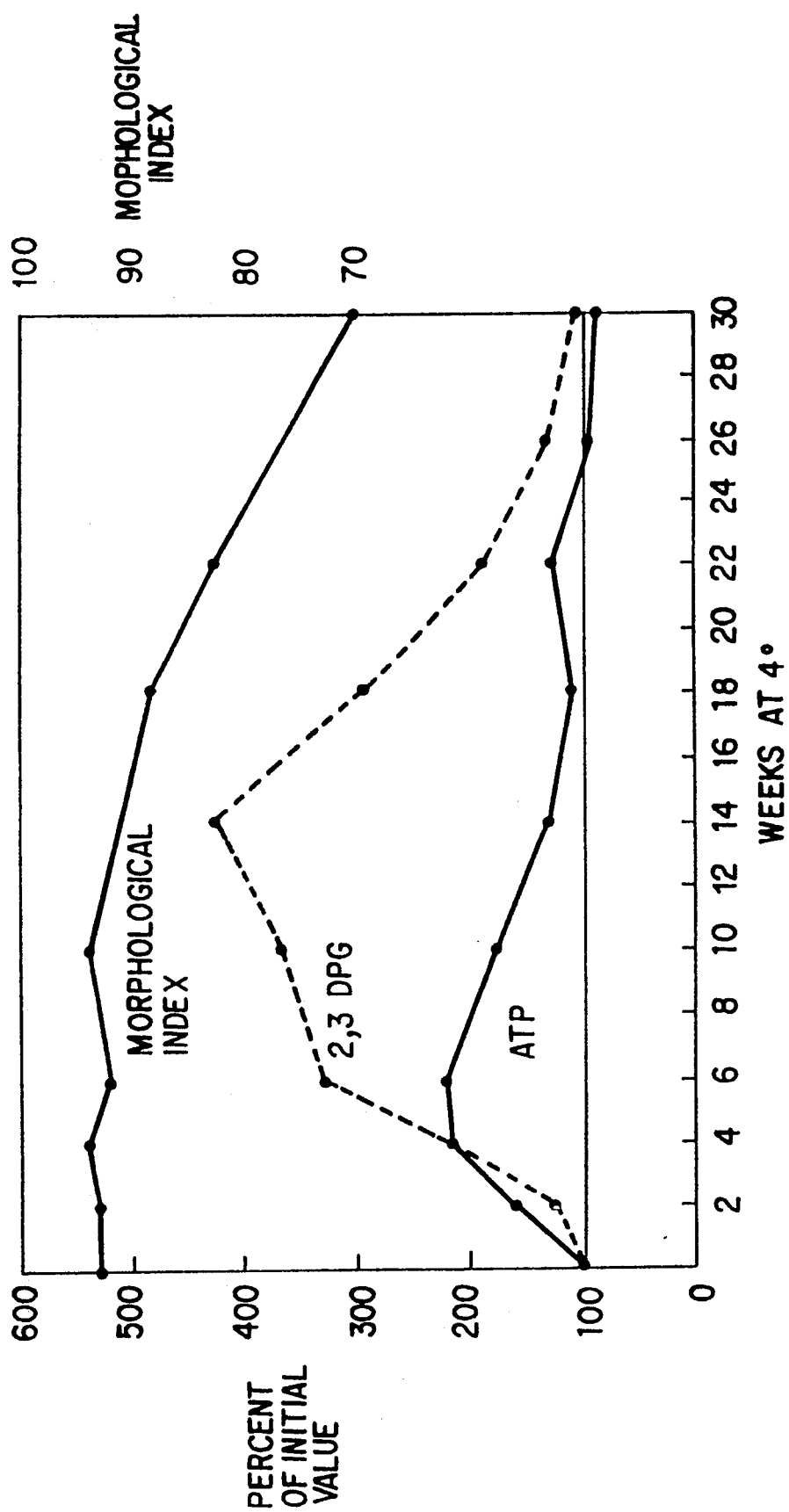

FIG. 16 illustrates the storage of red cells for non-clinical use, such as for typing panels, where storage conditions can be optimized without regard for the acceptability of the storage solution for transfusion. In this example, cells were stored at an hematocrit of 8% in a solution containing 1.6 g% sodium gluconate, a non-penetrating solute, and 0.66 g% dibasic ammonium phosphate, a superior buffer that penetrates the cells, in addition to glucose and adenine which are provided as substrate for glycolysis. The maintenance of ATP and 2,3 DPG for 30 weeks is unprecedented in the field of red cell storage and illustrates the potential of this invention.

Figure 17:
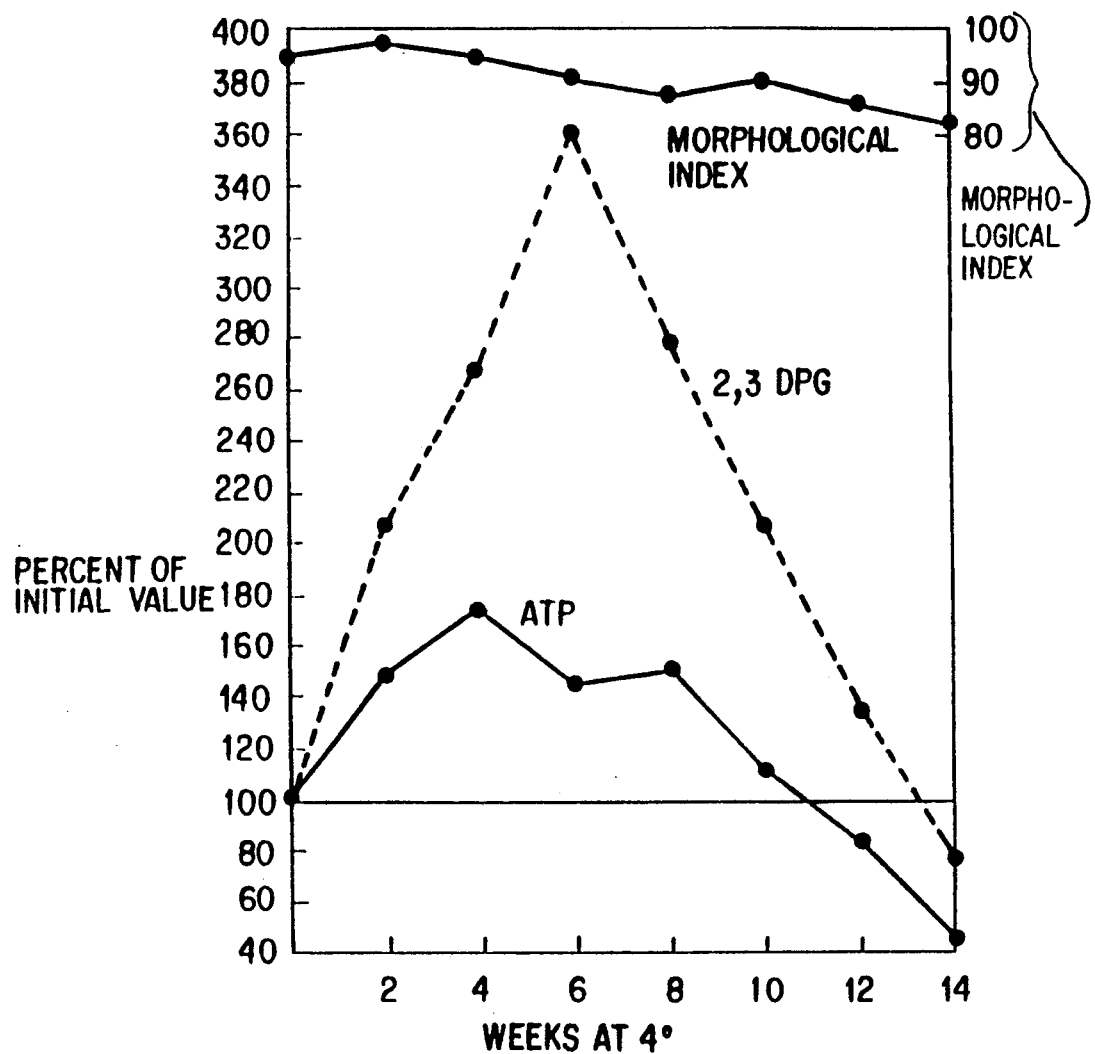

FIG. 17 illustrates the results of storing red cells prepared as in FIG. 15 but using a dilution solution containing one tenth the amount of adenine present in ARC30. The maintenance of ATP and morphological index is comparable to that shown in FIG. 15 but 2,3 DPG maintenance is markedly better, demonstrating not only that red cells stored in accordance with this invention do not require adenine in the concentrations conventionally used, but may even benefit from its absence.

DESCRIPTION OF THE PREFERRED EMBODIMENTS

Unless defined otherwise, all technical and scientific terms used herein have the same meaning as is commonly understood by one of ordinary skill in the art. All publications mentioned herein are incorporated by reference.

As used herein, improved prolonged shelf life or improved storage of red blood cells refers to the preservation of viable red blood cells for an extended period of time with low hemolysis and with cell morphological index and levels of ATP and 2,3 DPG that are greater than the levels of morphological index, ATP and 2,3 DPG in cells stored by the conventional methods known to those of skill in the art.

The terms are meant to apply to storage periods of about or greater than 30–60 days, in most cases greater than 90, or even greater than 120–160 days.

As used herein, storage at low hematocrit means storage at an hematocrit that is lower than 55%. Typically low hematocrit storage would take place at an hematocrit of between 5 and 10%.

As used herein, intracellular pH ($pH_i$) is the pH of the interior of a cell; whereas, extracellular pH ($pH_x$) is the pH of the medium in which said cells are maintained. Unless otherwise indicated, pH is measured at room temperature, about 22° C. Thus, when it is stated that the $pH_i$ is about 7.4, it is the $pH_i$ as measured at about 22° C. The pH of a solution is a temperature dependent parameter and the degree of temperature dependence, which can readily be measured, is a function of the particular solutes in the solution. It has been empirically determined that a $pH_i$ of 7.4 at about 22° C. for red blood cells is equivalent to a $pH_i$ of about 7.9 at about 4° C. and a $pH_x$ of 7.4 at 22° C. is equivalent to about 7.65 at about 4° C. Since cells in storage are at 4° C.±2° C., measurements of pH relating to stored cells are made at 4° C. and are so indicated in the text.

As used herein, a penetrating solute is a solute that is capable of freely traversing the cell membrane of red blood cells by passive diffusion. Such a solute may be either a small non-electrolyte such as glucose, or it may be a small anion such as chloride, acetate or phosphate. Non-penetrating solutes include larger non-electrolytes such as mannitol and sucrose, or large anions such as citrate, gluconate, and glycerophosphate. Cations, because of their charge, will not penetrate the cell membranes. An exception is the ammonium ion that enters the cell as the neutral molecule, ammonia, and reestablishes the ionized state inside the cell. (see, e.g. Meryman, H. T. (1973) *Am. J. Physiol.* 225:365-371).

As used herein, a biologically compatible solution or a biologically compatible buffered solution is a solution in which cells that are contacted therewith retain viability. Contacting includes any process in which the cells are in some manner exposed to the solution and includes, but is not limited to, suspension of the cells in the buffered solution. A biologically compatible buffered solution has a pH and has a salt concentration that is suitable for maintaining the integrity of the cell membrane and does not inhibit or destroy the biological and physiological reactions of the cells contacted therewith. Typically a biologically compatible buffered solution has a pH between 5 and 9.0 and is isotonic or only moderately hypotonic or hypertonic. Biologically compatible buffered solutions include, but are not limited thereto those listed in Table 1, infra.

As used herein, a biologically compatible buffered solution that raises the intracellular pH of red blood cells is a biologically compatible buffered solution that is prepared in accordance with this invention and that effects an increase in the intracellular pH of cells that are contacted therewith. Examples of biologically compatible buffered solution that raise the intracellular pH of a red blood cell, which are used in accordance with this invention, include, but are not limited to, solutions that contain substantially no chloride ion and that have a pH between 5 and 9.0, generally between 7.4 and 7.5. The solutions listed in Table 2, infra, such as ARC8, are examples of biologically compatible buffered solution that raise the intracellular pH of red blood cells that are contacted therewith.

TABLE 1

Biologically Compatible Buffered Solutions Currently Used for Cell Storage

| Ingredient | CPDA-1/ (mM) | ADSOL (mM) | NUTRICEL (mM) |
|---|---|---|---|
| NaCitrate | 89.6 | — | 20.0 |
| cit. acid | 15.6 | — | 2.0 |
| dextrose | 161.0 | 111.0 | 55.5 |
| $NaH_2PO_4$ | 16.1 | — | 20.0 |
| Adenine | 2.0 | 2.0 | 2.2 |
| Mannitol | — | 41.2 | — |
| NaCl | — | 154.0 | 70.1 |
| Osmolality (mOsm) | 323 | 342 | 244 |
| pH | 5.7 | 5.5 | 5.8 |

CDPA-1 and ADSOL are sold by Baxter Travenol and NUTRICEL is sold by Cutter.
Osmolality is the effective osmolality contributed by the non-penetrating constitients.

TABLE 2

Examples of Biologically Compatible Buffered Solutions That Can Effect an Increase in the Intracellular pH of Red Blood Cells

| Name | Ingredient | Concentration (mM) | Grams (%) | Osmolality (mOsm) | pH |
|---|---|---|---|---|---|
| ARC8 | glucose | 139 | 2.5 | 126 | 7.4 |
|  | NaCit. | 33.3 | 0.98 | (w/o |  |
|  | $Na_2HPO_4$ | 12.0 | 0.17 | glucose) |  |
|  | $NaH_2PO_4.H_2O$ | 2.9 | 0.04 |  |  |
|  | Adenine | 2.0 | 0.028 |  |  |
| ARC9C | glucose | 177.0 | 3.19 | 121 | 7.5 |
|  | NaCit. | 27.2 | 0.8 | (w/o |  |
|  | $Na_2HPO_4$ | 12.0 | 0.17 | glucose) |  |
|  | $NaH_2PO_4.H_2O$ | 2.9 | 0.04 |  |  |
|  | Adenine | 2.0 | 0.028 |  |  |
| ARC32 | glucose | 177.0 | 3.19 | 283 | 8.0 |
|  | NaCit. | 89 | 2.63 | (w/o |  |
|  | $Na_2HPO_4$ | 16 | 0.227 | glucose) |  |
|  | Adenine | 2.0 | 0.028 |  |  |
| ARC27 | glucose | 69 | 1.24 | 126 | 7.4 |
|  | NaCit. | 33.3 | 0.98 | (w/o |  |
|  | $Na_2HPO_4$ | 12.0 | 0.17 | glucose) |  |
|  | $NaH_2PO_4.H_2O$ | 2.9 | 0.04 |  |  |
|  | Adenine | 1.14 | 0.016 |  |  |
| ARC30 | glucose | 50 | 0.9 | 136 | 7.5 |
|  | NaCit. | 22.0 | 0.4 | (w/o |  |
|  | $Na_2HPO_4$ | 10.6 | 0.15 | glucose) |  |
|  | $NaH_2PO_4.H_2O$ | 2.5 | 0.04 |  |  |
|  | Adenine | 0.01 | 0.00014 |  |  |
|  | Mannitol | 44 | 0.8 |  |  |

As used herein, effective osmolality refers to the combined osmolality of solutes that do not penetrate the red cell membrane and therefore serve to determine the volume of the red cell.

In accordance with this invention, it has been discovered that when the chloride concentration can be reduced and the $pH_i$ can be raised to between about 7.4 and about 8.5, as measured at about 22° C., red blood cells can be stored for many weeks with both ATP and 2,3 DPG at or above normal levels and with excellent morphology and 24-hour in vivo survival. It has also been discovered in accordance with this invention, that the shelf life of red cells depends on the extent of the initial dilution of chloride, the elevation of $pH_i$ and the extent to which it can be maintained during storage by the inclusion of appropriate buffers in the storage solution.

In accordance with this invention, $pH_i$ may be increased by any means, whereby it is raised to levels above about 7.4, when measured at about 22° C. The intracellular pH ($pH_i$) of red blood cells may be adjusted to a level between about 7.0 to about 8.5. A particularly effective mechanism for achieving an initial elevation of $pH_i$ to this level is the chloride shift that occurs when cells are washed with solutions that contain impermeant anions or non-electrolytes. Under these circumstances, chloride is washed from the cell and, in the absence of a counter anion to replace intracellular chloride and in order to maintain charge neutrality, $OH^-$ enters the cell, thereby neutralizing the intracellular $H^+$ and raising $pH_i$. As demonstrated herein, a variety of wash solutions are able to manipulate both $pH_i$ and $pH_x$ with $pH_i$ under some circumstances elevated to above 8.0.

The $pH_i/pH_x$ differential that results from the chloride shift is maintained throughout the storage period as long as penetrating anions are not reintroduced. This means that maintenance of $pH_x$ by extracellular buffers helps to maintain $pH_i$ at a level at which effective glycolysis can proceed.

On the other hand, once $pH_i$ has been elevated, the intracellular hemoglobin, which is a strong buffer, tends to maintain the $pH_i$ even through chloride or some other penetrating anion may be reintroduced, effectively eliminating the $pH_i/pH_x$ differential.

Two factors are important for the maintenance of $pH_i$ during low temperature (e.g., 4° C.) storage: induction of the chloride shift that elevates the $pH_i$ and maximization of the buffering capacity of the suspending solution. During storage, the differential between $pH_i$ and $pH_x$ is maintained throughout the storage period as long as a penetrating anion is not reintroduced. The extracellular pH, $pH_x$, establishes the base upon which the $pH_i/pH_x$ is superimposed, so that maintaining $pH_x$ indirectly maintains $pH_i$. If the buffering capacity of the buffer is increased by, for example, increasing the quantity of buffer, $pH_i$ can be maintained for many weeks. This, in turn, leads to the maintenance of elevated levels of ATP and 2,3 DPG.

The dual objectives of maximizing chloride shift and maximizing buffering capacity can be achieved by storing red cells by a variety of means. It has been discovered that one effective means for doing so is to store the cells at a low hematocrit which provides a very large ratio of buffer to cells. Transfusable red cells can be recovered after more than fourteen weeks of refrigerated storage at low hematocrit. Cells suitable for use in typing panels can be recovered for use after at least thirty weeks of refrigerated storage.

The effective osmolality of the suspending solution is another factor of importance in extending red cell storage time. Effective osmolality refers to the osmolality of the solutes that do not penetrate the cell and thereby influence cell volume. It has been shown (Meryman, supra.) that effective hypotonicity substantially reduces storage hemolysis. Although the mechanism has not been proven, it is probable that osmotic swelling increases cell surface tension, thereby forestalling the shape changes usually associated with stored red cells. Regardless of the mechanism, storage hemolysis can be reduced many-fold by limiting the concentration of those extracellular solutes that do not penetrate the cell to an osmolality just short of hemolytic.

As has been reported by Meryman (supra.), when red cells are suspended in a solution comprised of solutes known as macromolecular stabilizers, including at least one solute that can penetrate the red cell, there is an increase in membrane area and red cells which usually start to hemolyze at 170 mOsm at a volume of about 120 $\mu^3$, can be suspended in solutions of osmolality as low as 80 mOsm and reach a volume of about 170 $\mu^3$ without hemolysing. The solutes used in this invention, primarily phosphate, citrate and glucose are all macromolecular stabilizers, with glucose a penetrating solute. It is therefore possible to take advantage of the membrane expansion phenonomenon to reduce the effective osmolality of a red cell storage solution to osmolalities below those normally considered hemolytic.

It has also bee found that, when red cells are stored according to this invention, adenine is no longer required as a substrate for glycolysis since glycolysis appears to be occurring under more or less physiological conditions and nucleotides are being recycled rather than consumed.

As a first step when practicing any of the embodiments of the invention disclosed herein for the storage of washed red cells, blood is drawn from a donor into a suitable solution known to those of skill in the art, such as CPDA-1, CDP or citrate anticoagulant, and the platelet-rich plasma is removed within 8 hours. The remaining red cells are washed or diluted until the amount of residual plasma is significantly reduced, using standard washing or dilution methods known to those of skill in the art.

For the storage of washed cells in accordance with the invention, the cells are washed with a biologically compatible buffered solution that effects an increase in intracellular pH of the cells. In order to effect the increase in the intracellular pH, the cells may be washed with a solution that is substantially free of chloride ion, that has a pH of at least about 7.4, and that has at least one non-penetrating anion or non-electrolyte in place of chloride ion.

Alternatively, rather than washing the cells, they may be diluted into or with a buffer that is substantially free of chloride anion or other penetrating anions and that contains non-penetrating or substantially non-penetrating anions or non-electrolyte in place thereof. Also contemplated to be within the scope of this invention are the use of any treatment means whereby the intracellular pH of red blood is raised prior to storage of said cells.

If the washed or treated red blood cells are to be stored in a solution that differs from the wash solution, the cells are sedimented using standard methods to a hematocrit that is generally greater than about 90, the supernatant is removed, and the cells are resuspended in an appropriate volume of the desired storage solution depending on the end use of the cell suspension.

In an embodiment in accordance with this invention where red blood cells are not washed, blood is drawn from the donor into an anticoagulant such as CPDA-1, CDP or a citrate solution adjusted to a pH of 7.0 or higher (7.0 to 8.5; preferably 7.4–7.5). Following collection of whole blood in the anticoagulant, the red cells are separated from the plasma by, for example, centrifuging the whole blood, at a relatively high force ("hard spin"), such as, but not limited to, about 7268 G for 10 minutes, whereby the red cells are packed at an hematocrit of about 90% or higher. The packed cells are resuspended in a suitable volume of an effectively hypotonic, biologically compatible buffer that is effective in maintaining a $pH_i$ of greater than about 7.4, such as ARC8. The final volume of the cell suspension is selected so that it is comparable to the volumes, typically 350 to 400 ml, conventionally used for storing transfusible red blood cells known to those of skill in the art. This procedure can yield storage characteristics for non-washed cells superior to any procedure previously reported.

In an another alternative embodiment of the invention, after collecting the blood in a suitable anticoagulant, such as CDP, CPDA-1, or citrate anticoagulant at any pH and removing the plasma, the red cells can be diluted to a low hematocrit by addition of a suitable amount, such as, but not limited to, about two liters, of an effectively hypotonic biologically compatible buffer, such as, but not limited to ARC8, that has a pH of at least about 7.0, and storing the cells at 4° C. for up to at least fourteen weeks.

Dilution for such storage may be accomplished by any acceptable means. For example, the red cells can be introduced into an elongated bag, and diluted with about 2 liters of a biologically compatible buffered solution that has a pH of at least about 7.0. During storage at 4° C., the bag can be hung in a vertical position. The cells settle to the bottom of the bag. If necessary, during storage the cells can be gently mixed. When it is time to transfuse the cells the settled cells can be removed from the bag by draining the cells out of the bottom of the bag and into a transfer pack or any other method that yields uncontaminated red cells that can be used for transfusion.

Prior to transfusion, the morphological index, the percentage of hemolysis, the intracellular pH, and the levels of ATP and 2,3 DPG of the stored cells may be measured.

The morphological index may be measured by any method known to those of skill in the art. For example, it can be measured by direct observation of the morphology of paraformaldehyde-fixed cells in the light microscope according to the procedure of Hogman et al. (Hogman, C. F., et al. (1980) *Hematologia* 13:135–144) in which the cells are scored according to the extent to which they depart from normal discoid shape.

The percentage of hemolysis may be measured by any method known to those of skill in the art. For example, samples of cells can be assayed for percent hemolysis with a hemoglobinometer (Coulter Electronics, Inc., Hialeah, FL.) using the following formula:

$$\% \text{ hemolysis} = 100 - \text{hematocrit} \times \frac{\text{supernatant hemoglobin concentration}}{\text{total hemoglobin concentration}}$$

The levels of ATP and 2,3 DPG may be measured by any method known to those of skill in the art. For example, red cells can be assayed for ATP and 2,3 DPG according to the methods described in Technical Bulletins 336-W and 35~(Sigma Chemical Co., St. Louis, Mo.) using a spectrophotometer, such the Model D~, (Beckman Instruments Inc., Fullerton, Calif.) and a recorder, such as the Model 2000 (Gilford Instrument Laboratories, Inc. Oberlin, Ohio).

The intracellular pH may be measured by any method known to those of skill in the art. In one such method the red blood cells are centrifuged at a sufficient acceleration to form a hard cell pellet. The supernatant is removed and the packed cells are sequentially frozen and thawed in order to hemolyze them. The pH of the hemolysate, which is the same as the intracellular pH of the cells, is measured. Generally, because of the dependence of pH on temperature, such measurements are conducted at 4° C., or are corrected for differences that are attributable to temperature.

The low hematocrit storage system also can be used for the storage of red cells for typing. Such cells are currently provided at low hematocrit with a shelf-life of approximately 30–40 days. For typing, hemolysis must not exceed 5%. Because there are no restrictions imposed on the constituents of the storage solution when the red cells are not to be transfused, any solute, which in accordance with this invention substantially increases shelf-life, may be used. These solutes include ammonium phosphate, sodium gluconate or sodium glycerophosphate. Ammonium phosphate enters the cells and is an excellent buffer, but has no osmotic effect. Sodium glycerophosphate and sodium gluconate do not penetrate the cell and, thus, maximize the chloride shift. Solutes such as these can be used and the shelf-life of blood used for typing can be extended for at least thirty weeks.

ARC8 also functions as a rejuvenation solution. Cells that have been stored in ADSOL for 42 days and then washed in ARC8 acquire an additional 5 weeks of storage time, thereby eliminating the need for incubation at 37° C. to achieve rejuvenation and subsequent freezing as currently practiced.

In a preferred embodiment using the methods of this invention, blood is drawn into CDP or citrate anticoagulant which has been adjusted to pH of 7.0 or higher. Within about 8 hours, the blood is sedimented at at least 7000 g for at least 10 min to create hard-packed red cells with an hematocrit of at least 90%, preferably 95 to 98%. The red cells are separated from the other blood components and resuspended in at least 100 ml, preferably between 150 and 200 ml, of ARC8. If resuspension is in more than 100 ml of ARC8, the concentration of the constituents of the solution should be reduced so that there is the same quantity of each as would have been present in 100 ml of ARC8. Red cells collected, separated and stored in this fashion have, after six weeks of storage, ATP, 2,3 DPG, morphological index, extracellular potassium concentration and hemolysis superior to cells collected and stored in conventional fashion.

Alternatively, after the plasma is removed, the cells are directly diluted into about two liters of ARC8 and stored at low hematocrit. More specifically, after component separation, packed red cells are added to two liters of ARC8 solution, which achieves a roughly tenfold dilution. This ten-fold dilution maximizes the chloride shift and reduces the effective osmolality of the extracellular solution. The more than ten-fold increase in the volume of the extracellular solution also provides a substantial reservoir of buffer, which maintains both $pH_i$ and $pH_x$ during storage. This method provides storage for at least 14 weeks.

The following examples are included for illustrative purposes only and are not intended to limit the scope of the invention.

EXAMPLE 1

Storage of Washed Cells 450 ml. of blood was drawn from a donor into 63 ml of CPDA-1. The platelet-rich plasma was removed. The remaining cells were divided into two equal aliquots into 400 ml. bags, and the bags were filled with washing solution, which was either a standard isotonic saline solution (0.9% NaCl) or a phosphate buffer solution at pH 7. The cells were then centrifuged at 1471 g for 5 minutes in a Sorvall PC3C clinical centrifuge and the washing step was repeated once. The concentration of residual plasma was reduced by a factor of about $10^2$.

Figure 1:
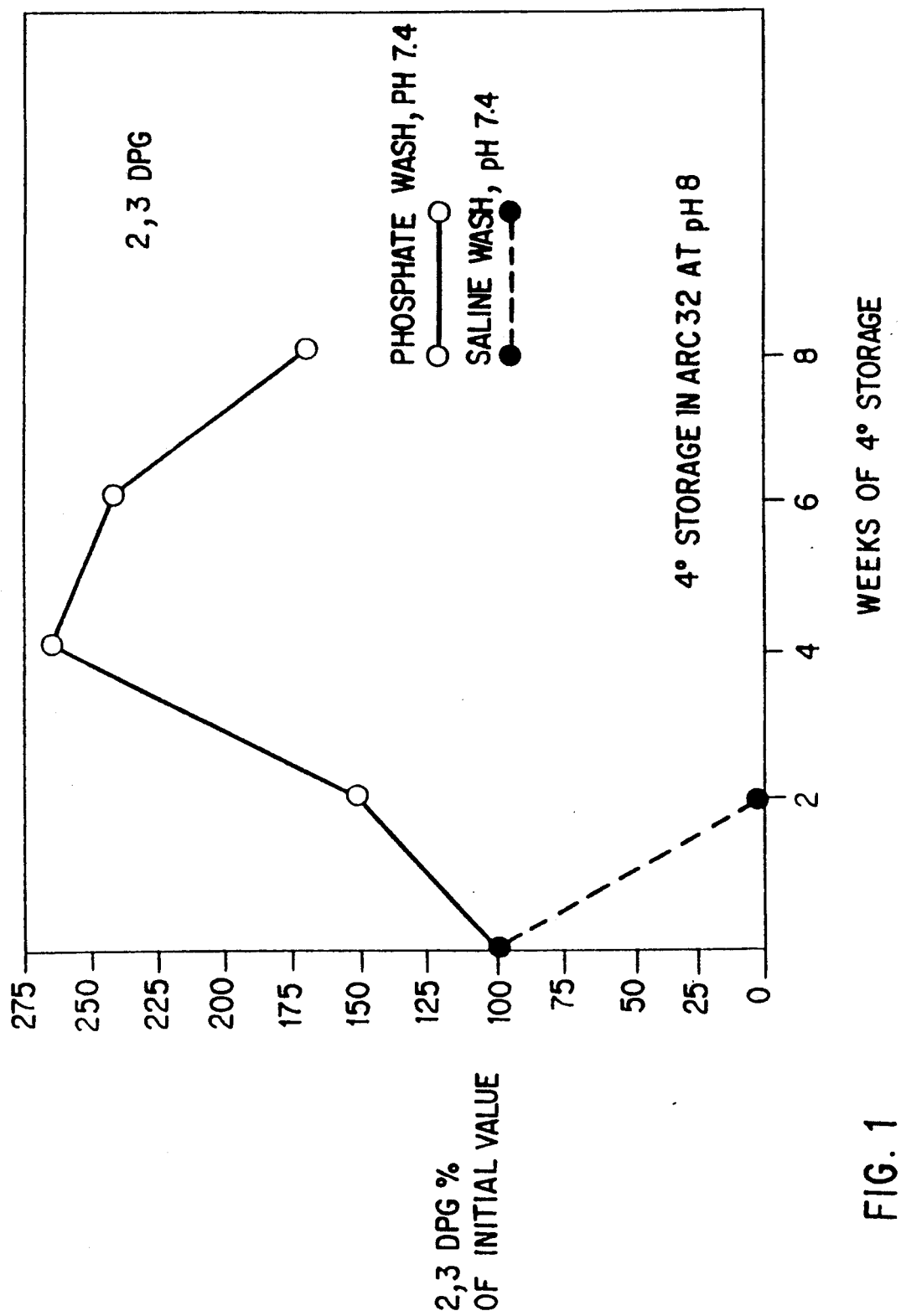
FIG. 1 depicts the percentage of 2,3 DPG in red blood cells, wherein 100% is the amount of 2,3 DPG in fresh red blood cells, during prolonged storage at 4° C.±2° C. in ARC32 after washing the cells in either phosphate wash at pH 7.4 -0-0-0-, or saline wash at pH 7.4.
Figure 2:
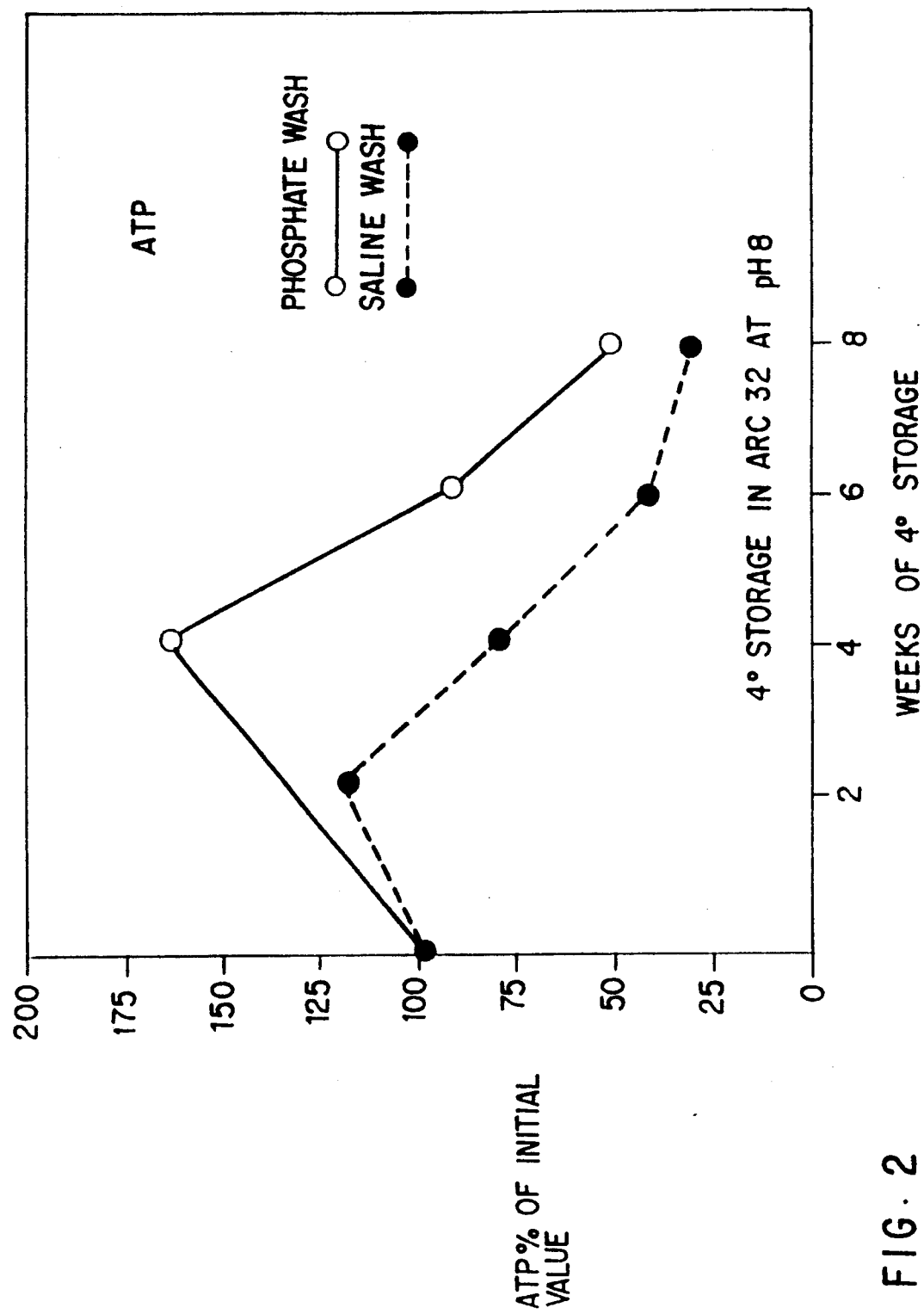
FIG. 2 depicts the percentage at ATP in red blood cells, wherein 100% is the amount of ATP in fresh red blood cells, during prolonged storage at 4° C.±2° C. in ARC32 after washing the cells in either phosphate wash at pH 7.4, 0--0--0--0-, or saline wash.
Figure 3:
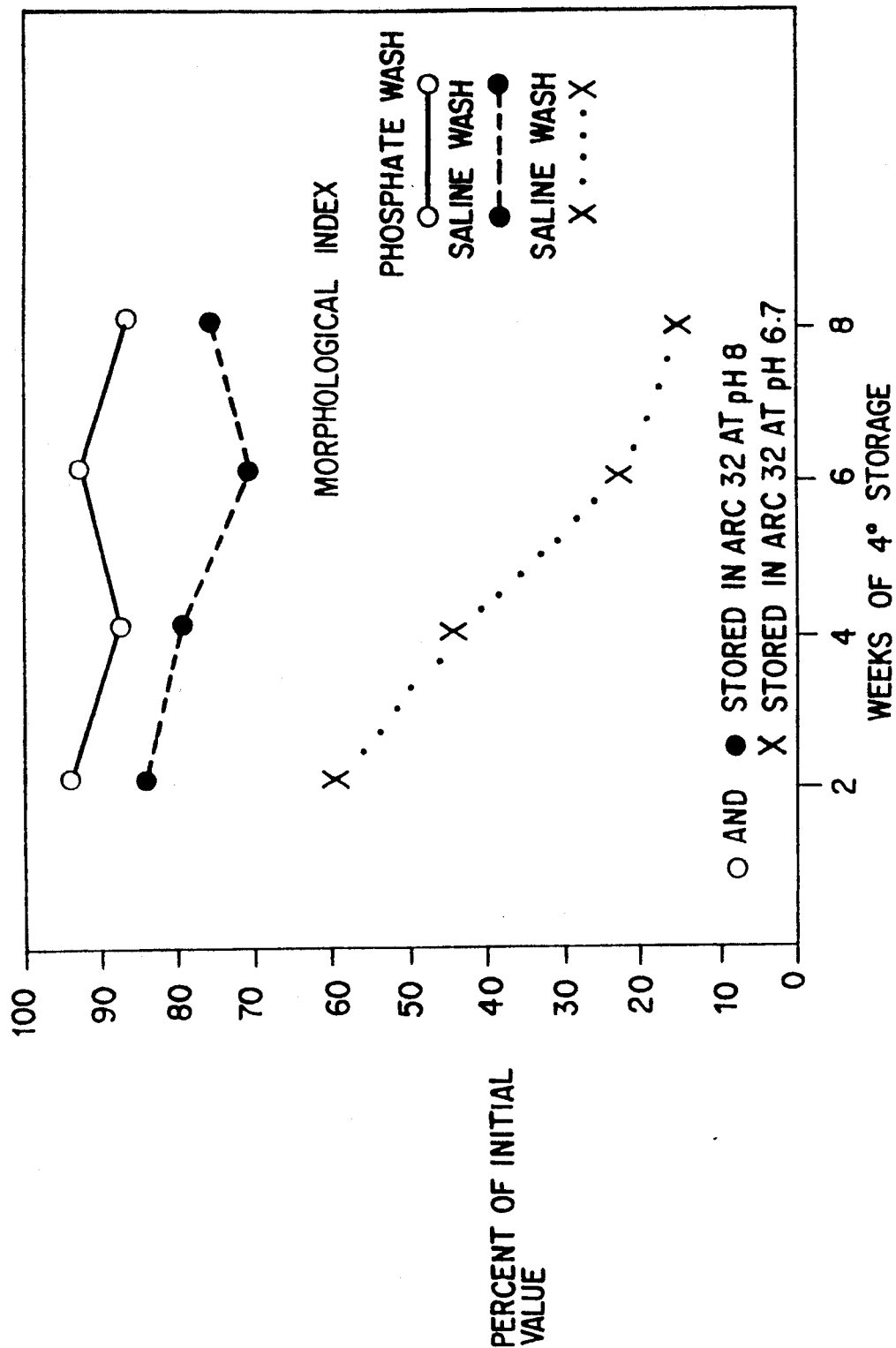
FIG. 3 depicts the morphological index of red blood cells during prolonged storage at 4° C.±2° C. in ARC32 after washing the cells in either phosphate wash at pH 7.4, -0--0--0-, or saline wash at pH 7.4, or during prolonged storage at 4° C.±2° C. in CPDA-1 at pH 5.7, after washing the cells in saline wash -X--X--X-.
Figure 4:
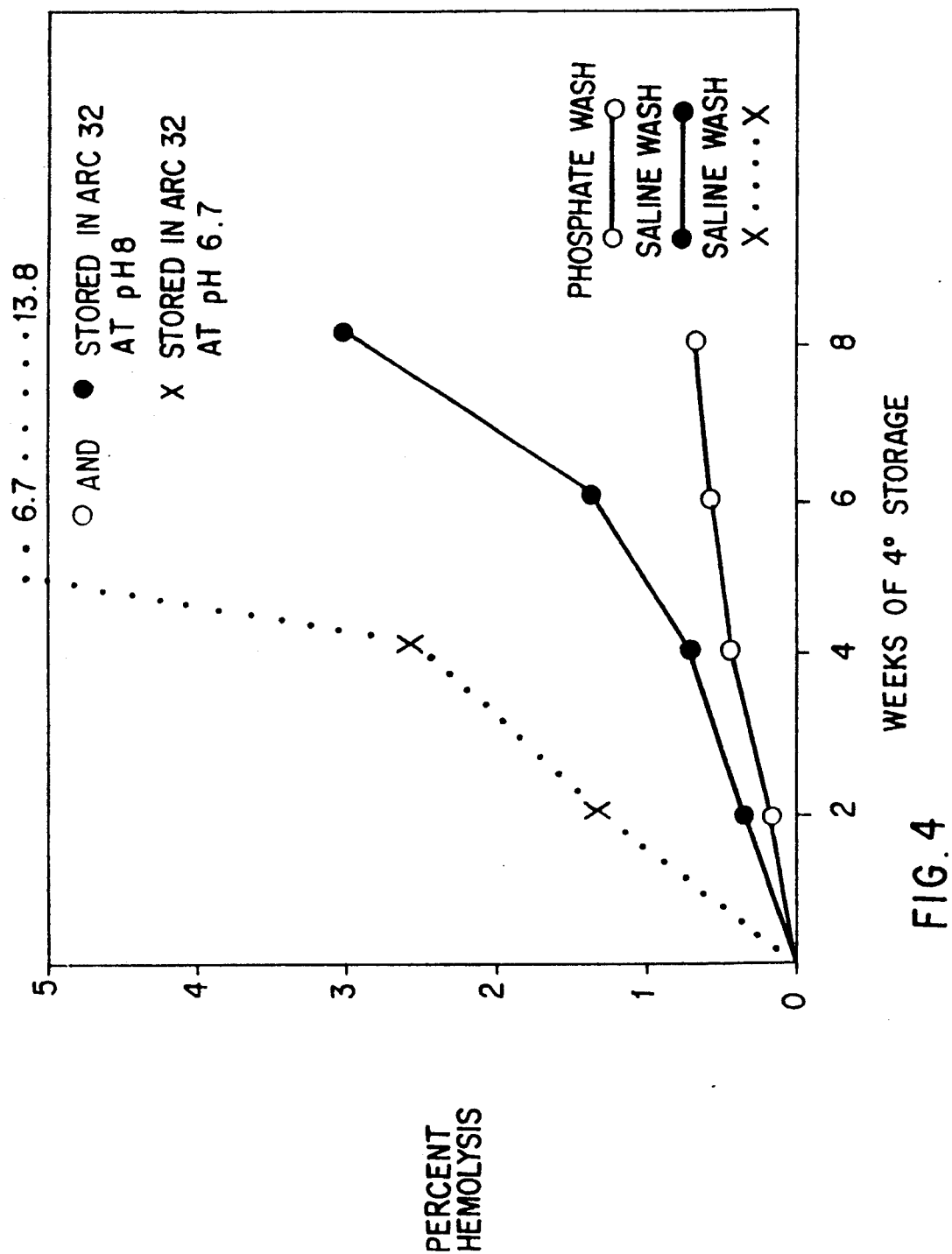
FIG. 4 depicts the percentage of hemolysis of red blood cells during prolonged storage at 4° C.±2° C. in ARC32 after washing the cells in either phosphate wash at pH 7.4, -0-0-0-, or saline wash at pH 7.4 or during prolonged storage at 4° C.±2° C. in CPDA-1, pH 5.7, after washing the cells in saline wash -X--X--X-.

After washing, the cells were again divided into two aliquots and were resuspended in either CPDA-1 at pH 5.7 or ARC32 at pH 8 to a hematocrit of about 45. The resuspended cells were stored at 4° C.+2° C. The stored cells were periodically sampled and the levels of 2,3 DPG and ATP and the morphological index and percentage hemolysis were measured. FIGS. 1–4 depict the results of these measurements. It can be seen that the cells that were washed with phosphate solution prior to storage had substantially higher levels of both ATP and 2,3 DPG (FIGS. 1 & 2), had a higher morphological index (FIG. 3), and a significantly lower percentage of hemolysis (FIG. 4) during the course of storage compared to the cells that were washed with saline. Further, it can be seen in FIG. 2 that the levels of 2,3 DPG in the cells that were washed in phosphate were substantially higher than the levels in fresh blood cells; whereas, the levels of 2,3 DPG in the saline washed cells rapidly decreased below the levels in fresh cells during the course of storage. Cells that were washed in saline and stored in a low pH solution, CPDA-1 at pH 5.7 in this example, show an even more rapid decline in morphological index (FIG. 3) and rise in hemolysis (FIG. 4).

EXAMPLE 2

Storage of Washed Cells

Figure 5:
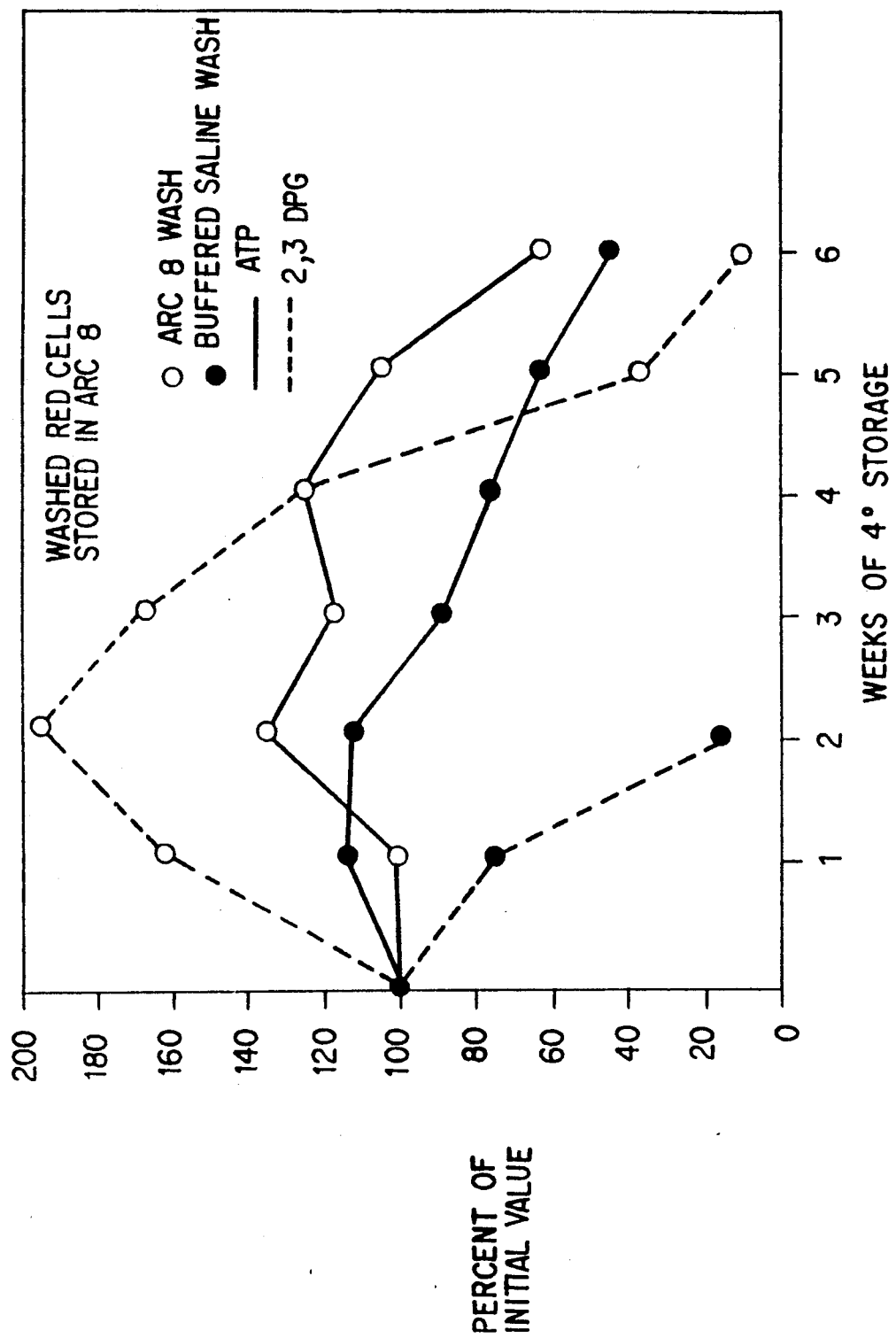
FIG. 5 depicts a comparison of the indices and percentages of ATP,    , and 2,3 DPG, - - - -, in red blood cells that have been washed in either ARC8, pH 7.5, -0-0-0-, or in phosphate buffered saline wash (154 mM NaCl, 2 mM $NaH_2PO_4$, 7.7 mM $Na_2HPO_4$), pH 7.31,    . and stored in ARC8, pH 7.5, at 4° C.±2° C. for 6 weeks. This figure demonstrates that even the addition of phosphate buffer to the saline wash fails to provide benefit in terms of ATP and 2,3 DPG maintenance when compared to a wash that both reduces chloride concentration and provides strong buffering at pH 7.4.

Blood was drawn as in Example 1. The red cells were divided into two aliquots and washed twice using two 10 minute cycles at 2995 g. in a Sorvall RC3C clinical centrifuge. The concentration of residual plasma was thereby reduced by a factor of about $10^3$. The washing solutions were either ARC8 or buffered saline (154 mM NaCl, 2.2 mM NaH$_2$PO$_4$, 7.75 mM Na$_2$HPO$_4$, pH 7.31). All cells were resuspended in ARC8 to an hematocrit of about 55 and stored at 4° C.±2° C. The stored cells were periodically sampled and the levels of 2,3 DPG and ATP were measured. The results of those measurements are shown in FIG. 5.

EXAMPLE 3

Storage of Washed Cells

Figure 6:
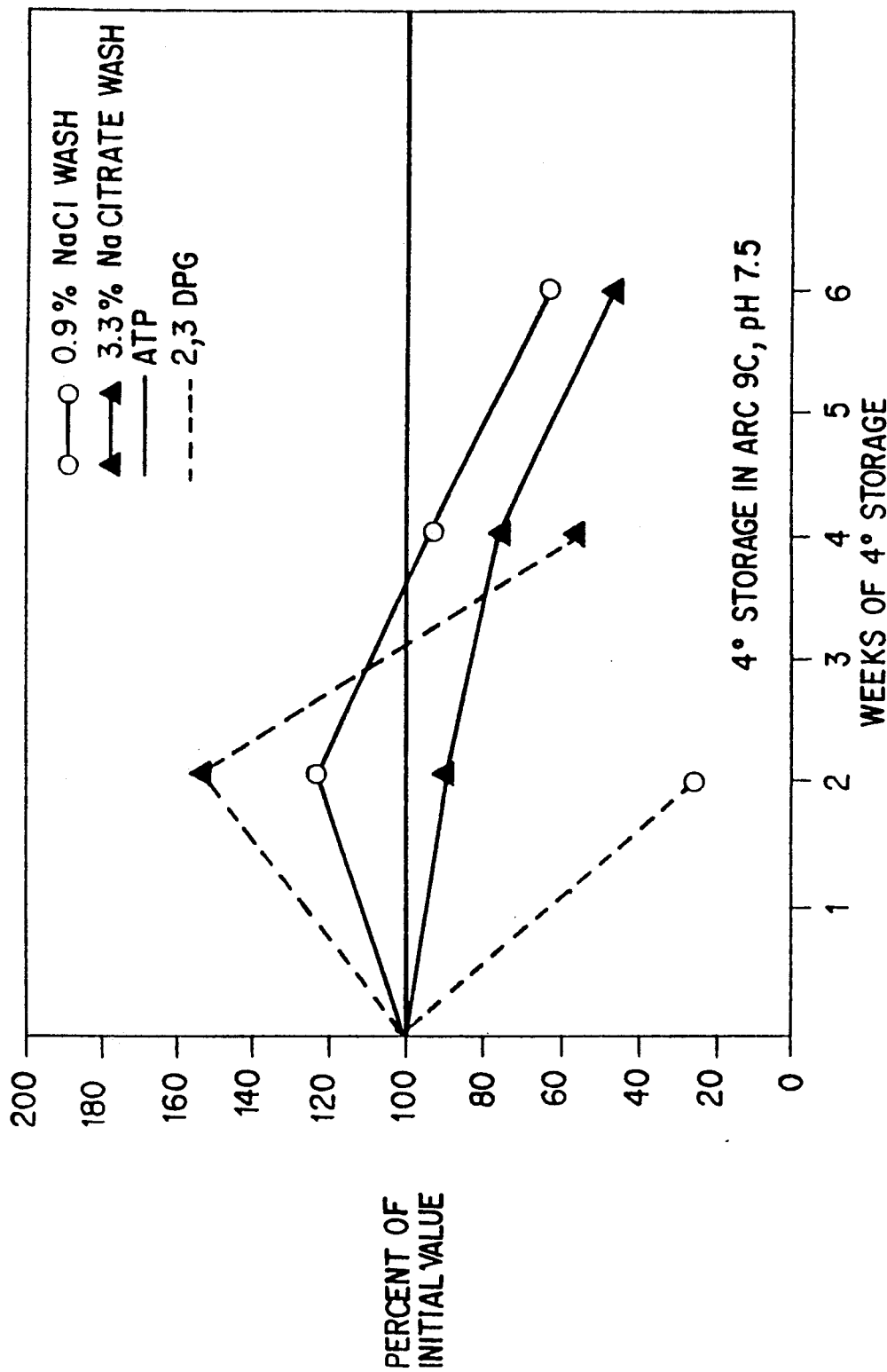
FIG. 6 depicts a comparison of the levels of ATP,    and of 2,3 DPG, - - - -, in red blood cells that had been washed in either saline wash, osmolality 286 and pH 7.4, or in sodium citrate (122 mM), osmolality 297, pH 7.39, and subsequently stored at 4° C.±2° C. in ARC9C, pH 7.5. This figure shows that even a wash with citrate, which has negligible buffering capacity at pH 7.4, is superior to a saline wash with respect to 2,3 DPG maintenance because of the chloride shift induced by this non-penetrating anion.

·Blood was drawn as in Example 1. The red cells were divided into two aliquots and washed once at 2995 g. in a Sorvall RC3C clinical centrifuge. The concentration of residual plasma was thereby reduced by a factor of about $10^2$. The washing solutions were either 154 mM NaCl or 112 mM sodium citrate, both at pH 7.4 and at isotonic osmolality. Following washing the cells were resuspended in ARC9C to an hematocrit of about 70 and were stored at 4° C.+2° C. The stored cells were periodically sampled and the levels of 2,3 DPG and ATP were measured. The results of those measurements are shown in FIG. 6.

EXAMPLE 4 pH Measurements

The intracellular and extracellular pH of fresh red blood cells that had been washed repeatedly with standard isotonic saline, pH 7.4, were measured and compared with the intracellular and extracellular pH of an aliquot of the same cells that had been washed repeatedly with isotonic sodium citrate, pH 7.4. The intracellular pH of the saline washed cells was 7.3 and the extracellular pH was 7.47. In contrast, the intracellular pH of cells that had been washed with chloride free sodium citrate was 8.11 and the extracellular pH was 7.07. All pH measurements were made at 22° C.

EXAMPLE 5

One unit of blood was drawn as in Example 1. The red cells were repeatedly washed with an isotonic sodium citrate solution at pH 7.4.

Each wash diluted the concentration of diffusible ions, including chloride, by a factor of 2.5. After each wash, the extracellular and intracellular pH of an aliquot were measured. As shown in FIG. 7, as the cells were successively washed, the intracellular pH increased and the extracellular pH decreased. The greatest differential between intracellular and extracellular pH was observed at the point at which the chloride concentration was reduced to approximately 10% of its initial value. As washing continued, the extracellular and intracellular pH increased, but the magnitude of the differential was constant.

The same experiment was performed using isotonic sodium phosphate buffer, pH 7.4, for washing the cells. The results of this experiment are shown in FIG. 8. Because phosphate diffuses into the cell the ability of isotonic sodium phosphate buffer to induce a differential between the extracellular and intracellular pH is thereby limited. Because of its buffering capacity, however, it is a suitable buffer for storage because intracellular pH does rise to a reasonable level for maintenance of ATP and 2,3 DPG levels.

FIG. 9 illustrates the results of combining the effect of citrate on chloride shift with the buffering capacity of phosphate. Both chloride shift and buffering are apparent when the cell suspension was progressively diluted with ARC8.

EXAMPLE 6

Cells, prepared as in Example 5, were first washed in a solution of 112 mM (isotonic) sodium citrate solution at pH 7.4 and then in a solution of 154 mM (isotonic) sodium chloride, pH 7.4 Because hemoglobin is an excellent buffer in the range pH 7.0–8.0, it was found that after the $pH_i/pH_x$ differential was maximized by washing in a solution that included a non-penetrating anion, the resulting high intracellular pH was retained even after the cells were resuspended in a solution that contained a penetrating ion (see FIG. 10).

Thus, the elevation of the pH of intracellular hemoglobin is important for maintaining a relatively high intracellular pH, which, as demonstrated in Examples 2–4, contributing to the maintenance of intracellular levels of ATP and 2,3-DPG during long-term storage.

EXAMPLE 7

Cells, prepared as in Example 5, were first washed in a solution that contained isotonic (171 mM) sodium phosphoglycerate which is both non-penetrating and a good buffer in the pH range 7.0 to 8.0. Following the third wash, the cells were washed in ARC8, which is acceptable for transfusion. As shown in FIG. 11, this protocol results in an initial high intracellular pH and a large intracellular pH/extracellular pH differential and the high $pH_i$ is maintained after washing with ARC8.

EXAMPLE 8

Effect of Osmolality

To demonstrate the importance of effective hypotonicity in the storage of red cells, a unit of blood was drawn into CPDA-1 and the red cells separated by soft spin. The resulting red cells were then divided into two equal aliquots. One was washed and stored in ARC8, effective osmolality 126 mOsm. The other was washed and stored in ARC8 made isotonic (300 mOsm) with mannitol. There was no significant difference in the ATP and 2,3 DPG maintenance during storage. However, as shown in FIG. 12, the morphological index and hemolysis were strikingly better in the hypotonic preparation.

EXAMPLE 9

Storage of Washed Cells

Eight units of blood were drawn into CPDA-1 and the red cells separated by hard spin. Each unit of red cells was then washed twice in ARC8 using a hard spin and stored in ARC8 for seven weeks. As is evident from FIG. 13, the $pH_i/pH_x$ differential is maintained throughout the storage period, 2,3 DPG remains above normal, ATP is well maintained and, most significant, the morphological index remains above 90%.

In six paired studies in volunteers who received either conventional cells stored in Adsol or cells washed and stored in ARC8, the mean 24-hour in vivo survival, using a single-label $^{51}$chromium tag, was 74.8±5.7% for units stored for 6 weeks in Adsol and was 87.1±6.3 for units washed and stored for 6 weeks in ARC8.

EXAMPLE 10

Storage of Non-washed Cells

A unit of blood was drawn into 63 ml. of 3.5% sodium citrate, pH 7.4, spun down hard, and resuspended in 170 ml ARC27, pH 7.4 The $pH_i$, was 7.9. The chloride concentration was 34 mM, approximately one tenth of that prior to dilution. The change in morphological index and the percentage of initial intracellular concentrations of 2,3 DPG and ATP as a function of weeks of storage at 4° C. is shown in FIG. 14.

EXAMPLE 11

Storage at Low Hematocrit

Blood was drawn in CDPA-1 anticoagulant and diluted in about 2 liters of ARC30, pH 7.5, in an elongated bag. The morphological index, and the percentage of initial intracellular concentrations of 2,3 DPG and ATP as a function of weeks of storage at 4° C. at an hematocrit of 10% are shown in FIG. 15. At 14 weeks the $pH_i$ remained above 7.0 and the hemolysis was less than 1%.

EXAMPLE 12

Red cells were stored at an hematocrit of approximately 8% in a solution containing sodium gluconate, which is non-penetrating and maximizes chloride shift and ammonium phosphate, a good buffer in the pH range 7.0–8.0 and which also penetrates the cell, thus contributing its buffering capacity to both the intracellular and extracellular spaces. As shown in FIG. 16, even after 30 weeks of refrigerated storage, 2,3 DPG remained above the initial value indicating normal glycolysis. ATP was 60% of initial, the morphological index was 70% and hemolysis was less than 5%. These cells would be acceptable for use in typing panels.

EXAMPLE 13

Storage at Low Adenine Concentrations

Red cells were washed once and stored in ARC8 with the adenine concentration reduced to 0.2 mM, one tenth of the usual concentration. As shown in Table 3, by the second week, this small amount of adenine had been completely consumed, yet ATP, 2,3 DPG and morphological index were satisfactorily maintained for up to 7 weeks. $pH_i$ remained above 7.0 at 7 weeks. It is apparent from these data that red cells washed or diluted according to this invention do not require adenine as an exogenous substrate for glycolysis.

TABLE 3

|  | Weeks at 4° C. | | | | | | |
|---|---|---|---|---|---|---|---|
|  | 1 | 2 | 3 | 4 | 5 | 6 | 7 |
| *ATP | 4.1 | 4.1 | 3.6 | 3.4 | 2.9 | 2.5 | 2.4 |
| *2,3 DPG | 15.6 | 19.5 | 18.8 | 18.1 | 15.6 | 11.1 | 7.2 |
| *Adenine | 0.4 | 0.0 | — | — | — | — | — |
| Morphological Index | 92 | 97 | 93 | 92 | 88 | 94 | 94 |
| $pH_i$ | 7.45 | 7.2 | 7.06 | 7.2 | 7.0 | 6.95 | 7.1 |

*μM/gm Hgb

EXAMPLE 14

Red cells were prepared and diluted in two liters of ARC30 as in Example 11 but with adenine reduced to a concentration of only 1 μM. As shown in FIG. 17, reduction in the adenine concentration had no significant effect on ATP and morphological index and 2,3 DPG maintenance was substantially improved.

Since modifications will be apparent to those of skill in the art, it is intended that this invention be limited only by the scope of the appended claims.

We claim:

1. A method for prolonging the storage shelf life of transfusible red blood cells, comprising:
    (a) adjusting the intracellular pH of said cells to a level between about 7.0 to about 8.5 by washing or diluting the cells in a biologically compatible buffered solution comprising an impermeant anion or an impermeant non-electrolyte, wherein said intracellular pH is adjusted by decreasing the intracellular chloride concentration; and
    (b) storing said cells in a biologically compatible buffered solution.

2. A method for prolonging the storage shelf life of transfusible red blood cells, comprising:
    (a) adjusting the intracellular pH of said cells to a level between about 7.0 to about 8.5, wherein said intracellular pH is adjusted by washing said cells with an effectively hypotonic, biologically buffered solution, at a pH of about 7.0 to about 8.5, and which solution lacks chloride ions; and (b) storing said cells in a biologically compatible buffered solution.

3. A method for prolonging the storage shelf life of transfusible red blood cells, comprising:

(a) adjusting the intercellular pH of said cells to a level between about 7.0 to about 8.5, wherein said intracellular pH is adjusted by diluting said cells with an effectively hypotonic, biologically compatible buffered solution, at a pH of about 7.0 to about 8.5, and which solution lacks chloride ions; and (b) storing said cells in a biologically compatible buffered solution.

4. A method for prolonging the storage shelf life of transfusible red blood cells, comprising:

(a) adjusting the intracellular pH of said cells to a level between about 7.0 to about 8.5 by washing or diluting the cells in a biologically compatible buffered solution comprising an impermeant anion or an impermeant non-electrolyte; and (b) storing said cells in a biologically compatible buffered solution that lacks chloride ions.

5. A method for prolonging the storage shelf life of transfusible red blood cells, comprising:

(a) adjusting the intracellular pH of said cells to a level between about 7.0 to about 8.5; and (b) storing said cells in a biologically compatible buffered solution that comprises impermeable solutes having an effective osmolality that is hypotonic.

6. A method for prolonging the storage shelf life of transfusible red blood cells, comprising:

(a) adjusting the intracellular pH of said cells to a level between about 7.0 to about 8.5 by washing or diluting the cells in a biologically compatible buffered solution comprising an impermeant anion or an impermeant non-electrolyte; and (b) storing said cells in a biologically compatible buffered solution that has little or no adenine.

7. A method for prolonging the storage shelf life of transfusible red blood cells, comprising:

(a) adjusting the intracellular pH of said cells to a level between about 7.0 to about 8.5; and (b) storing said cells in a biologically compatible buffered solution at low hematocrit.

8. A method for prolonging the storage shelf life of transfusible red blood cells, comprising:

(1) drawing whole blood into an anticoagulant solution;

(2) separating red blood cells form plasma; and (3) washing said separated cells with an effectively hypotonic, biologically compatible buffered solution capable of adjusting the intracellular pH of said cells to a level between about 7.0 to about 8.5, and which solution lacks chloride ions.

9. The method of claim 8 which after the step (3) comprises:

(4) separating said washed cells from said wash solution of step (3); and (5) storing said washed separated cells in a biologically compatible buffered solution.

10. The method of claim 9, wherein said separation step (4) is carried out to a hematocrit greater than about 90.

11. A method for prolonging the storage shelf life of transfusible red blood cells, comprising:

(1) drawing whole blood into an anticoagulant solution;

(2) separating red blood cells form plasma; and (3) diluting said cells with an effectively hypotonic, biologically compatible buffered solution capable of adjusting the intracellular pH of said cells to a level between about 7.0 to about 8.5, and which solution lacks chloride ions.

12. The method of claim 11 which after step (3) comprises:

(4) storing said diluted cells in said dilution buffer of step (3).

13. A method for prolonging the storage shelf life of transfusible red blood cells, comprising:

(1) drawing whole blood into an anticoagulant solution at a pH of from 7.0 to 8.5;

(2) separating red blood cells from plasma at a hard spin whereby said cells are packed at a hematocrit of greater than about 90; and (3) resuspending said packed cells in an effectively hypotonic, biologically compatible buffered solution capable of adjusting the intracellular pH of said cells to a level between about 7.0 to about 8.5, and which solution lacks chloride ions.

14. A method for prolonging the storage shelf life of transfusible red blood cells, comprising:

(a) adjusting the intracellular pH of said cells to a level between about 7.0 to about 8.5; and (b) storing said cells in a biologically compatible buffered solution that is selected from the group consisting of ARC8, ARC9C, ARC32, ARC27 and ARC30.

* * * * *